(12) United States Patent
Letai et al.

(10) Patent No.: US 10,761,086 B2
(45) Date of Patent: Sep. 1, 2020

(54) HIGH THROUGHPUT BH3 PROFILING: A RAPID AND SCALABLE TECHNOLOGY TO BH3 PROFILE ON LOW NUMBERS OF CELLS

(71) Applicant: Dana-Farber Cancer Institute, Inc., Boston, MA (US)

(72) Inventors: Anthony Letai, Medfield, MA (US); Patrick Bhola, Cambridge, MA (US); Jeremy Ryan, Somerville, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 195 days.

(21) Appl. No.: 15/568,994

(22) PCT Filed: Apr. 27, 2016

(86) PCT No.: PCT/US2016/029495
§ 371 (c)(1),
(2) Date: Oct. 24, 2017

(87) PCT Pub. No.: WO2016/176288
PCT Pub. Date: Nov. 3, 2016

(65) Prior Publication Data
US 2018/0128813 A1 May 10, 2018

Related U.S. Application Data

(60) Provisional application No. 62/153,475, filed on Apr. 27, 2015.

(51) Int. Cl.
*G01N 1/00* (2006.01)
*G01N 33/50* (2006.01)

(52) U.S. Cl.
CPC ..... *G01N 33/5014* (2013.01); *G01N 33/5011* (2013.01); *G01N 33/5044* (2013.01); *G01N 33/5079* (2013.01); *G01N 2333/47* (2013.01); *G01N 2500/10* (2013.01); *G01N 2800/52* (2013.01)

(58) Field of Classification Search
CPC .............................. G01N 33/5014; G01N 1/00
USPC ........................................................... 435/29
See application file for complete search history.

(56) References Cited

U.S. PATENT DOCUMENTS

| | | | |
|---|---|---|---|
| 4,522,811 A | 6/1985 | Eppstein et al. |
| 4,676,980 A | 6/1987 | Segal et al. |
| 4,816,567 A | 3/1989 | Cabilly et al. |
| 4,946,778 A | 8/1990 | Ladner et al. |
| 5,225,539 A | 7/1993 | Winter |
| 5,545,806 A | 8/1996 | Lonberg et al. |
| 5,545,807 A | 8/1996 | Surani et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,674,980 A | 10/1997 | Frankel et al. |
| 5,804,604 A | 9/1998 | Frankel et al. |
| 5,916,771 A | 6/1999 | Hori et al. |
| 5,939,598 A | 8/1999 | Kucherlapati et al. |
| 5,965,703 A | 10/1999 | Horne et al. |
| 7,064,193 B1 | 6/2006 | Cory et al. |
| 7,714,005 B2 | 5/2010 | Chen et al. |
| 7,868,133 B2 | 1/2011 | Korsmeyer et al. |
| 8,221,966 B2 | 7/2012 | Letai |
| 9,360,473 B2 | 6/2016 | Cardone et al. |
| 9,540,674 B2 | 1/2017 | Letai |
| 9,856,303 B2 | 1/2018 | Korsmeyer et al. |
| 9,902,759 B2 | 2/2018 | Korsmeyer et al. |
| 10,393,733 B2 | 8/2019 | Letai et al. |
| 2002/0115613 A1 | 8/2002 | Kumar |
| 2004/0171809 A1 | 9/2004 | Korsmeyer et al. |
| 2007/0027175 A1 | 2/2007 | Shaughnessy et al. |
| 2008/0199890 A1 | 8/2008 | Letai |
| 2008/0234201 A1 | 9/2008 | Korsmeyer et al. |
| 2010/0286057 A1 | 11/2010 | Walensky et al. |
| 2011/0130309 A1 | 6/2011 | Cardone |
| 2011/0154522 A1 | 6/2011 | Korsmeyer et al. |
| 2013/0122492 A1 | 5/2013 | Khosravi et al. |
| 2013/0149718 A1 | 6/2013 | Letai |
| 2015/0362479 A1 | 12/2015 | Letai et al. |
| 2016/0200786 A1 | 7/2016 | Korsmeyer et al. |
| 2016/0231314 A1 | 8/2016 | Ryan et al. |
| 2016/0258933 A1 | 9/2016 | Letai |
| 2017/0160267 A9 | 6/2017 | Letai |
| 2017/0184567 A1 | 6/2017 | Letai |
| 2018/0120297 A1 | 5/2018 | Letai et al. |

(Continued)

FOREIGN PATENT DOCUMENTS

| | | |
|---|---|---|
| JP | H10-510059 A | 9/1998 |
| JP | 2005-130867 | 5/2005 |
| JP | 2005-518393 A | 6/2005 |

(Continued)

OTHER PUBLICATIONS

Emerman et al (In Vitro Cellular & Developmental Biology, 1987, 23(2): 134-139).*
U.S. Appl. No. 10/658,028, filed Sep. 9, 2003, Abandoned, 2004-0171809.
U.S. Appl. No. 11/789,557, filed Apr. 24, 2007, Granted, U.S. Pat. No. 7,868,1331.
U.S. Appl. No. 12/966,821, filed Dec. 13, 2010, Granted, U.S. Pat. No. 9,856,303.
U.S. Appl. No. 15/073,356, filed Mar. 17, 2016, Allowed, 2016-0200786.
U.S. Appl. No. 15/869,537, filed Jan. 12, 2018, Pending.

(Continued)

*Primary Examiner* — Sean E Aeder
(74) *Attorney, Agent, or Firm* — Wolf, Greenfield & Sacks, P.C.

(57) ABSTRACT

The present invention relates provides methods of predicting cell sensitivity to a test agent. In some embodiments, the cells are cultured in a culture medium having serum.

14 Claims, 28 Drawing Sheets

Specification includes a Sequence Listing.

(56) References Cited

U.S. PATENT DOCUMENTS

2018/0244740 A1     8/2018    Korsmeyer et al.

FOREIGN PATENT DOCUMENTS

| | | |
|---|---|---|
| JP | 2006-520606 | 9/2006 |
| JP | 2009-532033 A | 9/2009 |
| JP | 2009-240173 | 10/2009 |
| JP | 2009-542195 A | 12/2009 |
| JP | 2009-543044 | 12/2009 |
| JP | 2012-529890 | 11/2012 |
| JP | 2014-81365 | 5/2014 |
| WO | WO 91/00360 A1 | 1/1991 |
| WO | WO 92/20373 A1 | 11/1992 |
| WO | WO 93/08829 A1 | 5/1993 |
| WO | WO 94/02602 A1 | 2/1994 |
| WO | WO 94/11026 A2 | 5/1994 |
| WO | WO 96/27011 A1 | 9/1996 |
| WO | WO 96/33735 A1 | 10/1996 |
| WO | WO 96/34096 A1 | 10/1996 |
| WO | WO 97/05265 A1 | 2/1997 |
| WO | WO 99/53049 A1 | 10/1999 |
| WO | WO 00/59526 A1 | 10/2000 |
| WO | WO 01/12661 A2 | 2/2001 |
| WO | WO 02/20568 A2 | 3/2002 |
| WO | WO 03/040168 A2 | 5/2003 |
| WO | WO 2004/022580 A2 | 3/2004 |
| WO | WO 2004/058804 A1 | 7/2004 |
| WO | WO 2005/044839 A2 | 5/2005 |
| WO | WO 2006/099667 A1 | 9/2006 |
| WO | WO 2007/123791 A2 | 11/2007 |
| WO | WO 2007/149270 A2 | 12/2007 |
| WO | WO 2008/021484 A2 | 2/2008 |
| WO | WO 2010/147961 A1 | 12/2010 |
| WO | WO 2013/170176 A2 | 11/2013 |
| WO | WO 2013/188978 A1 | 12/2013 |
| WO | WO 2014/047342 A1 | 3/2014 |
| WO | WO 2015/010094 A1 | 1/2015 |
| WO | WO 2015/042249 A1 | 5/2015 |
| WO | WO 2016/176288 A1 | 11/2016 |
| WO | WO 2016/176299 A1 | 11/2016 |

OTHER PUBLICATIONS

U.S. Appl. No. 11/695,321, filed Apr. 2, 2007, Granted, U.S. Pat. No. 8,221,966.
U.S. Appl. No. 13/478,831, filed May 23, 2012, Granted, U.S. Pat. No. 9,540,674.
U.S. Appl. No. 15/073,391, filed Mar. 17, 2016, Published, 2016-0258933.
U.S. Appl. No. 15/335,238, filed Oct. 26, 2016, Published, 2017-0184567.
U.S. Appl. No. 14/429,272, filed Mar. 18, 2015, Allowed, 2015-0362479.
U.S. Appl. No. 15/022,987, filed Mar. 18, 2016, Published, 2016-0231314.
U.S. Appl. No. 15/569,851, filed Oct. 27, 2017, Published, 2018-0120297.
EP03749602.3, Jun. 7, 2006, Supplementary Partial European Search Report.
EP03749602.3, Sep. 28, 2006, Supplementary Partial European Search Report.
PCT/US2003/028482, Dec. 8, 2005, International Search Report.
PCT/US2007/008055, Jan. 2, 2008, International Search Report and Written Opinion.
PCT/US2007/008055, Sep. 30, 2008, International Preliminary Report on Patentability.
PCT/US2013/060707, Jan. 9, 2014, International Search Report and Written Opinion.
PCT/US2013/060707, Apr. 2, 2015, International Preliminary Report on Patenability.
EP14845952.2, Mar. 27, 2017, Extended European Search Report.
PCT/US2014/056284, Dec. 31, 2014, Inernational Search Report and Written Opinion.
PCT/US2014/056284, Mar. 31, 2016, International Preliminary Report on Patentability.
PCT/US2016/029495, Aug. 5, 2016, International Search Report and Written Opinion.
EP16787039.3, Oct. 4, 2018, Extended European Search Report.
PCT/US2016/029495, Nov. 9, 2017, International Preliminary Report on Patentability.
PCT/US2016/029510, Aug. 12, 2016, International Search Report and Written Opinion.
PCT/US2016/029510, Nov. 9, 2017, International Preliminary Report on Patentability.
Supplementary Partial European Search Report for EP03749602.3 dated Jun. 7, 2006.
Supplementary Partial European Search Report for EP03749602.3 dated Sep. 28, 2006.
International Search Report for PCT/US2003/028482 dated Dec. 8, 2005.
International Search Report and Written Opinion for PCT/US2007/008055 dated Jan. 2, 2008.
International Preliminary Report on Patentability for PCT/U2007/008055 dated Sep. 30, 2008.
International Search Report and Written Opinion for PCT/US2013/060707 dated Jan. 9, 2014.
International Preliminary Report on Patentability for PCT/US2013/060707 dated Apr. 2, 2015.
Extended European Search Report for EP14845952.2 dated Mar. 27, 2017.
International Search Report and Written Opinion for PCT/US2014/056284 dated Dec. 31, 2014.
International Preliminary Report on Patentability for PCT/US2014/056284 dated Mar. 31, 2016.
Extended European Search Report for EP16787039.3 dated Oct. 4, 2018.
International Search Report and Written Opinion for PCT/US2016/029495 dated Aug. 5, 2016.
International Preliminary Report on Patentability for PCT/US2016/029495 dated Nov. 9, 2017.
International Search Report and Written Opinion for PCT/US2016/029510 dated Aug. 12, 2016.
International Preliminary Report on Patentability for PCT/US2016/029510 dated Nov. 9, 2017.
Adams, et al., The Bcl-2 Protein Family: Arbiters of Cell Survival. Science. 1998;281(5381):1322-1326.
Ait-Ikhlef et al. The motoneuron degeneration in the wobbler mouse is independent of the overexpression of a Bcl2 transgene in neurons. Neurosci. Lett. 1995;199:163-6.
Bae et al., Underphosphorylated BAD interacts with diverse antiapoptotic Bcl-2 family proteins to regulate apoptosis. Apoptosis. 2001;6:319-30.
Barretina, J. et al. The Cancer Cell Line Encyclopedia enables predictive modeling of anticancer drug sensitivity. Nature 483 (7391), 2012, 603-607.
Bouillet et al., Proapoptotic Bcl-2 Relative Bim Required for Certain Apoptotic Responses, Leukocyte Homeostasis, and to Preclude Autoimmunity. Science. 1999;286:1735-8.
Boyd et al., Bik, a novel death-inducing protein shares a distinct sequence motif with Bcl-2 family proteins and interacts with viral and cellular survival-promoting proteins. Oncogene. 1995;11:1921-8.
Brady et al., Reflections on a peptide. Nature. 1994;368:692-3.
Brennan et al., Preparation of Bispecific Antibodies by Chemical Recombination of Monoclonal Immunoglobulin $G_1$ Fragments. Science. 1985;229:81.
Buron, N. et al., Use of human cancer cell lines mitochondria to explore the mechanisms of BH3 peptides and ABT-737-induced mitochondrial membrane permeabilization. PLoS One. Mar. 31, 2010;5(3):e9924. doi:10.1371/journal.pone.0009924.
Calin et al., A MicroRNA Signature Associated with Prognosis and Progression in Chronic Lymphocytic Leukemia. N. Engl. J. Med. 2005;353:1793-801.

(56) References Cited

OTHER PUBLICATIONS

Campos et al., Method for monitoring of mitochondrial cytochrome c release during cell death: Immunodetection of cytochrome c by flow cytometry after selective permeabilization of the plasma membrane. Cytometry Part A. Jun. 2006;69(6):515-23.
Caron et al., Engineered Humanized Dimeric Forms of IgG Are More Effective Antibiotics. J. Exp. Med. 1992;176:1191-5.
Cartron et al., The first α Helix of Bax Plays a Necessary Role in Its Ligand-Induced Activation by the BH3-Only Proteins Bid and PUMA. Mol. Cell 2004;16:807-18.
Certo et al., Mitochondria Primed by Death Signals Determine Cellular Addiction to Antiapoptotic BCL-2 Family Members. Cancer Cell. May 2006;9:351-65.
Chen et al., Caspase cleavage of Bim$_{EL}$ triggers a positive feedback amplification of apoptotic signaling. Proc. Natl. Acad. Sci. USA. 2004;101(5):1235-40.
Chen et al., Differential Targeting of Prosurvival Bcl-2 Proteins by Their BH3-Only Ligands Allows Complementary Apoptotic Function. Mol. Cell. 2005;17:393-403.
Cheng et al., Bax-independent inhibition of apoptosis by Bcl-X$_L$. Nature. 1996;379:554-6. Abstract only.
Cheng et al., BCL-2, BCL-X$_L$ Sequester BH3 Domain-Only Molecules Preventing BAX- and BAK-Mediated Mitochondrial Apoptosis. Mol. Cell. 2001;8:705-11.
Chipuk et al., Direct Activation of Bax by p53 Mediates Mitochondrial Membrane Permeabilization and Apoptosis. Science. 2004;303:1010-4. Abstract only.
Chittenden et al., A conserved domain in Bak, distinct from BH1 and BH2, mediates cell death and protein binding functions. EMBO J. 1995;14(22):5589-96.
Chittenden et al., Induction of apoptosis by the Bcl-2 homologue Bak. Nature. 1995;374(6524):733-6. Abstract only.
Chonghaile et al., Pretreatment mitochondrial priming correlates with clinical response to cytotoxic chemotherapy. Science. Nov. 25, 2011;334(6059):1129-33. doi: 10.1126/science.1206727. Epub Oct. 27, 2011.
Cole et al., The EBV-Hybridoma technique and its application to human lung cancer. Monoclonal Antibodies and Cancer Therapy. 1985:77-96.
Cory et al., The Bcl2 Family: Regulators of the Cellular Life-Or-Death Switch. Nat. Rev. Cancer. 2002;2(9):647-56. Abstract only.
Cosulich et al., Regulation of apoptosis by BH3 domains in a cell-free system. Curr. Biol. 1997;7(12):913-20.
Cote et al., Generation of human monoclonal antibiotics reactive with cellular antigens. Proc. Natl. Acad. Sci. USA. 1983;80:2026-30.
Czabotar et al., Bax Activation by Bim? Cell Death and Differentiation. Sep. 2009;16:1187-91.
Davids et al., BH3 profiling demonstrates that restoration of apoptotic priming contributes to increased sensitivity to PI3K inhibition in stroma-exposed chronic lymphocytic leukemia cells. Blood 118(21). Nov. 18, 2011. Abstract only.
Davids et al., Targeting the B-cell lymphoma/leukemia 2 family in cancer. J Clin Oncol. Sep. 1, 2012;30(25):3127-35. doi: 10.1200/JCO.2011.37.0981. Epub May 29, 2012.
Degrado, Designs of peptides and proteins. Adv Protein Chem. 1988;39:51-124.
Deng et al., BH3 Profiling Identifies Three Distinct Classes of Apoptotic Blocks to Predict Response to ABT-737 and Conventional Chemotherapeutic Agents. Cancer Cell. Aug. 2007;12:171-85.
Derenne et al., Antisense strategy shows that Mcl-1 rather than Bcl-2 or Bcl-xL is an essential survival protein of human myeloma cells. Blood. 2002;100:194-9.
Desagher et al., Bid-induced Conformational Change of Bax Is Responsible for Mitochondrial Cytochrome c Release during Apoptosis. J. Cell Biol. 1999;144(5):891-901.
Di Lisa et al., Mitochondrial Function and Cell Injury in Single Cardiac Myocytes Exposed to Anoxia and Reoxygenation. Transplant Proc. 1995;27(5):2829-30.
Di Lisa et al., Mitochondrial membrane potential in single living adult rat cardiac myocytes exposed to anoxia or metabolic inhibition. J. Physiol. 1995;486(1):1-13.
Dohner et al., Genomic Aberrations and Survival in Chronic Lymphocytic Leukemia. N. Engl. J. Med. 2000;343:1910-16.
Egle et al., Bim is a suppressor of Myc-induced mouse B cell leukemia. Proc. Natl. Acad. Sci. USA. 2004;101(16):6164-9.
Ellerby, et al., Anti-cancer activity of targeted pro-apoptotic peptides. Nat. Med. 1999;5(9):1032-8.
Elliott et al., Intercellular Trafficking and Protein Delivery by a Herpesvirus Structural Protein. Cell. 1997;88:223-33.
Eskes et al., Bid Induces the Oligomerization and Insertion of Bax into the Outer Mitochondrial Membrane. Mol. Cell. Biol. 2000;20(3):929-35.
Fanidi et al., Cooperative interaction between c-myc and bcl-2 proto-oncogenes. Nature. 1992;359:554-6.
Fishwild et al., High-avidity human IgGk monoclonal antibodies from a novel strain of minilocus transgenic mice. Nature Biotechnology. 1996;14:845-51.
Frankel et al., Activity of synthetic peptides from the Tat protein of human immunodeficiency virus type 1. Proc. Natl. Acad. Sci. USA. 1989;86:7397-401.
Friedman, A. Precision medicine for cancer with next-generation functional diagnostics. Nat. Rev. Cancer 15 (12), Dec. 2015, 747-756.
Fuchs et al., Pathway for Polyarginine Entry into Mammalian Cells. Biochemistry Mar. 2004;43(9):2438-44.
Futaki et al., Arginine-rich Peptides: An Abundant Source of Membrane-Permeable Peptides Having Potential as Carriers for Intracellular Protein Delivery. J. Biol. Chem. 2001;276(8):5836-40.
Green et al., A matter of life and death. Cancer Cell. 2002;1:19-30.
Green et al., The Pathophysiology of Mitochondrial Cell Death. Science. 2004;305:626-9.
Green, Life, Death, BH3 Profiles, and the Salmon Mousse. Cancer Cell. Aug. 2007;12:97-9.
Griffiths et al., Cell Damage-induced Conformational Changes of the Pro-Apoptotic Protein Bak In Vivo Precede the Onset of Apoptosis. J. Cell Biol. 1999;144(5):903-14.
Gross et al., Enforced dimerization of BAX results in its translocation, mitochondrial dysfunction and apoptosis. EMBO J. 1998;17(14):3878-85.
Grosschedl et al., Introduction of a µ immunoglobulin gene into the mouse germ line: specific expression in lymphoid cells and synthesis of functional antibody. Cell. 1984;38:647-58.
Gruber et al., Efficient Tumor Cell Lysis Mediated by a Bispecific Single Chain Antibody Expressed in *Escherichia coli*. J. Immunol. 1994;152:5368-74.
Gul et al., Apoptotic blocks and chemotherapy resistance: strategies to identify Bcl-2 protein signatures. Briefings in Functional Genomics and Proteomics. Jan. 2008;7(1):27-34.
Hanahan et al., Heritable formation of pancreatic β-cell tumors in transgenic mice expressing recombinant insulin/simian virus 40 oncogenes. Nature. 1985;315:115-22.
Hanahan et al., The Hallmarks of Cancer. Cell. 2000;100:57-70.
Hans et al., Beta-carbolines induce apoptosis in cultured cerebellar granule neurons via the mitochondrial pathway. Neuropharmacology. Jan. 2005;48(1):105-17.
Harada et al., Survival factor-induced extracellular signal-regulated kinase phosphorylates BIM, inhibiting its association with BAX and proapoptotic activity. Proc. Natl. Acad. Sci. USA. 2004;101(43):15313-7.
Hemann et al., Evasion of the p53 tumour surveillance network by tumour-derived MYC mutants. Nature. 2005;436:807-11.
Hemann et al., Suppression of tumorigenesis by the p53 target PUMA. Proc. Natl. Acad. Sci. USA. 2004;101(25):9333-8.
Hengartner et al., *C. elegans* Cell Survival Gene ced-9 Encodes a functional Homolog of the Mammalian Proto-Oncogene bcl-2. Cell. 1994;76:665-76.
Holinger et al., Bak BH3 Peptides Antagonize Bcl-xL Function and Induce Apoptosis through Cytochrome c-independent Activation of Caspases. J. Biol. Chem. 1999;274(19):13298-304.
Holliger et al., Diabodies: Small bivalent and bispecific antibody fragments. Proc. Natl. Acad. Sci. USA. 1993;90:6444-8.

(56) References Cited

OTHER PUBLICATIONS

Hoogenboom et al., By-passing Immunisation, Human Antibodies from Synthetic Repertoires of Germline VH Gene segments rearranged in Vitro. J. Mol. Biol. 1992;227:381-8.
Hopp et al., Prediction of protein antigenic determinants from amino acid sequences. Proc. Natl. Acad. Sci. USA. 1981;78:3824-8.
Hsu et al., Nonionic Detergents Induce Dimerization among Members of the Bcl-2 Family. J. Biol. Chem. 1997;272(21):13829-34.
Huang et al., BH3-Only Proteins—Essential Initiators of Apoptotic Cell Death. Cell. 2000;103:839-42.
Huse et al., Generation of a large Combinatorial Library of the Immunoglobulin Repertoire in Phage Lambda. Science. 1989;246:1275-81.
Inohara et al., Harakiri, a novel regulator of cell death, encodes a protein that activates apoptosis and interacts selectively with survival-promoting proteins Bcl-2 and Bcl-$X_L$. Embo J. 1997;16(7):1686-94.
Jackson et al., Heat shock induces the release of fibroblast growth factor 1 from NIH 3T3 cells. Proc. Natl. Acad. Sci. USA. 1992;89:10691-5.
Jameson et al., A rationally designed CD4 analogue inhibits experimental allergic encephalomyelitis. Nature. 1994;368:744-6.
Jones et al., Nature, Replacing the complementarily-determining regions in a human antibody with those from a mouse. 1986;321:522-5.
Jonkers et al., Oncogene addiction: Sometimes a temporary slavery. Cancer Cell. 2004;6:535-8.
Kelekar et al., Bad is a BH3 Domain-Containing Protein that Forms an Inactivating Dimer with Bcl-$X_L$. Mol. Cell Biol. 1997;17(12):7040-6.
Kelekar et al., Bcl-2-family proteins: the role of the BH3 domain in apoptosis. Trends Cell Biol. 1998;8:324-30.
Kohler et al., Continuous cultures of fused cells secreting anti-body of predefined specificity. Nature. 1975;256:495-7.
Korsmeyer, S. et al., Pro-apoptotic cascade activates BID, which oligomerizes BAK or BAX into pores that result in the release of cytochrome c. Cell Death Differ. Dec. 2000;7(12):1166-73.
Kostelny et al., Formation of a Bispecific antibody by the Leucine Zippers. J. Immunol. 1992;148(5):1547-53.
Kozbor et al., The production of monoclonal antibodies from human lymphocytes. Immunol Today. 1983;4:72-9.
Kozbor, A human hybrid Myeloma for production of human monoclonal antibodies. J. Immunol. 1984;133:3001-5.
Krieg, Mechanisms and applications of immune stimulatory CpG oligodeoxynucleotides. Biochim Biophys Acta. 1999;1489(1):107-16.
Kuwana et al., BH3 Domains of BH3-Only Proteins Differentially Regulate Bax-Mediated Mitochondrial Membrane Permeabilization Both Directly and Indirectly. Mol. Cell. 2005;17:525-35.
Kuwana et al., Bid, Bax, and Lipids Cooperate to Form Supramolecular Openings in the Outer Mitochondrial Membrane. Cell. 2002;111:331-42.
Kyte et al., A Simple Method for displaying the Hydropathic Character of a protein. J. Mol. Biol. 1982;157:105-42.
La Vieira, et al., Cell permeable BH3-peptides overcome the cytoprotective effect of Bcl-2 and Bcl-$X_L$. Oncogene. 2002;21(13):1963-77.
Leo et al., Characterization of the Antiapoptotic Bcl-2 Family Member Myeloid Cell Leukemia-1 (Mcl-1) and the Stimulation of Its Message by Gonadotropins in the Rat Ovary. Endocrinol. 1999;140(12):5469-77.
Letai et al., Antiapoptotic BCL-2 is required for maintenance of a model leukemia. Cancer Cell. 2004;6:241-9.
Letai et al., Distinct BH3 domains either sensitize or activate mitochondrial apoptosis, serving as prototype cancer therapeutics. Cancer Cell. Sep. 2002;2(3):183-92.
Letai, BH3 domains as BCL-2 inhibitors: prototype cancer therapeutics. Expert Opin Biol Ther. Apr. 2003;3(2):293-304.
Letai, The BCL-2 network: Mechanistic insights and therapeutic potential. Drug Disc. Today: Disease Mechanisms. 2005;2(2):145-51.

Letai, A. Perturbing cancer cell mitochondria to learn how to kill cancer with BH3 profiling. Broad Institute, Seminar Series on Cell Circuits and Epigenetics. Jul. 28, 2014 Presentation.
Li et al., Cleavage of BID by Caspase 8 Mediates the Mitochondrial Damage in the Fas Pathway of Apoptosis. Cell. 1998;94(4):491-501.
Li et al., Endonuclease G is an apoptotic DNase when released from mitochondria. Nature. 2001;412:95-9.
Li et al., tsg 101: A novel tumor susceptibility gene isolated by controlled Homozygous functional knockout of Allelic Loci in Mammalian Cells. Cell. 1996;85:319-29.
Liu et al., Bax conformational change is a crucial step for PUMA-mediated apoptosis in human leukemia. Biochem Biophys Res Commun. 2003;310(3):956-62.
Lonberg et al., Antigen-specific human antibodies from mice comprising four distinct genetic modifications. Nature. 1994;368:856-9.
Lonberg et al., Human Antibodies from Transgenic Mice. Intern Rev Immunol. 1995;13:65-93.
Long, J. et al., Optimization and validation of mitochondria-based functional assay as a useful tool to identify BH3-like molecules selectively targeting anti-apoptotic Bcl-2 proteins. BMC Biotechnol. May 24, 2013;13:45. doi: 10.1186/1472-6750-13-45.
Luo et al., Bid, a Bc12 interacting protein, mediates cytochrome c release from mitochondria in response to activation of cell surface death receptors, Cell. 1998;94(4):481-90.
Lutter et al., The pro-apoptotic Bcl-2 family member tBid localizes to mitochondrial contact sites. BMC Cell Biology. 2001;2:22.
Marani et al., Identification of Novel Isoforms of the BH3 Domain Protein Bim which Directly Activate Bax to Trigger Apoptosis. Mol Cell Biol. 2002;22(11):3577-89.
Marks et al., By-passing Immunization human Antibodies from v-gene libraries displayed on phage. J. Mol. Biol. 1991;222:581.
Marks et al., By-passing immunization: building high affinity human antibodies by chin shuffling. Bio/Technology. 1992;10:779-83.
Martin, Opening the Cellular Poison Cabinet. Science. Dec. 2010;330:1330-1.
Mason et al., The Hypogonadal mouse: reproductive functions restored by gene therapy. Science. 1986;234:1372-8.
Matsushita et al., A high-efficiency protein transduction system demonstrating the role of PKA in long-lasting long-term potentiation. J. Neuroscience. 2001;21(16):6000-7.
Matsuzaki, Why and how are peptide-lipid interactions utilized for self-defense? Biochem. Soc. Transactions. 2001;29:598-601.
Mcdonnell et al., bcl-2-Immunoglobulin Transgenic Mice Demonstrate Extended B Cell Survival and Follicular Lymphoproliferation. Cell. 1989;57:79-88.
Means et al., Modifications to change properties in Chemical Modification of Protein. 1974. Chapter 3, pp. 35-54, Holden-Day.
Milstein et al., Hybrid hybridomas and their use in immunohistochemistry. Nature. 1983;305:537-9.
Montero et al., Drug-induced death signaling strategy rapidly predicts cancer response to chemotherapy. Cell. Feb. 26, 2015;160(5):977-90. doi:10.1016/j.cell.2015.01.042.
Morrison et al., Success in specification. Nature. 1994;368:812-3.
Muchmore et al., X-ray and NMR structure of human Bcl-xL, an inhibitor of programmed cell death. Nature. 1996;381:335-41.
Munson et al., LIGAND: A Versatile Computerized Approach for Characterization of Ligand-Binding Systems. Analytical Biochemistry. 1980;107:220-39.
Nakano et al., PUMA, a Novel Proapoptotic Gene, is Induced by p53. Mol. Cell. 2001;7:683-94.
Narita, et al., bax interacts with the permeability transition pore to induce permeability transition and cytochrome c release in isolated mitochondria. Proc. Natl. Acad. Sci. USA. 1998;95:14681-6.
Neuberger et al., Generating high-avidity human Mabs in mice. Nature Biotechnology. 1996;14:826.
O'Brien et al., Phase I and II Multicenter Study of Oblimersen Sodium, a Bcl-2 Antisense Oligonucleotide, in Patients With Advanced Chronic Lymphocytic Leukemia. J. Clin. Oncol. 2005;23(30):7697-702.
O'Connor et al., Bim: a novel member of the Bcl-2 family that promotes apoptosis. Embo J. 1998;17(2):384-95.

(56) References Cited

OTHER PUBLICATIONS

Oda et al., Noxa, a BH3-Only Member of the Bcl-2 Family and Candidate Mediator of p53-Induced Apoptosis. Science. 2000;288:1053-8.
Oh et al., Conformational Changes in BID, a Pro-apoptotic BCL-2 Family Member, upon Membrane Binding. J. Biol. Chem. 2005;280(1):753-67.
Oliver, C. et al., Permeabilization of Cell Membranes. C. Oliver and M.C. Jamur (eds.), Immunocytochemical Methods and Protocols, Methods in Molecular Biology, vol. 588, DOI 10.1007/978-1-59745-324-0_9, © Humana Press, a part of Springer Science + Business Media, LLC 1995, 1999, 2010. Chapter 9: 4 pages.
Oltersdorf et al., An inhibitor of Bcl-2 family proteins induces regression of solid tumours. Nature. 2005;435:677-81.
Opferman et al., Development and maintenance of B and T lymphocytes requires antiapoptotic MCL-1. Nature. 2003;426:671-6.
Pinkert et al., An albumin enhancer located 10 kb upstream functions along with its promoter to direct efficient, liver-specific expression in transgenic mice. Genes and Dev. 1987;1:268-276.
Polster et al., BH3 Death Domain Peptide Induces Cell Type-selective Mitochondrial Outer Membrane Permeability. J. Biol. Chem. 2001;276 (41):37887-94.
Presta, Antibody engineering. Curr. Op. Struct. Biol. 1992;2:593-6.
Putcha et al., Induction of BIM, a Proapoptotic BH3-Only BCL-2 Family Member, Is Critical for Neuronal Apoptosis. Neuron. 2001;29(3):615-28.
Puthalakath et al., Bmf: a Proapoptotic BH3-Only Protein Regulated by Interaction with the Myosin V Actin Motor Complex, Activated by Anoikis. Science. 2001;293:1829-32.
Puthalakath et al., Keeping killers on a tight leash: transcriptional and post-translational control of the pro-apoptotic activity of BH3-only proteins. Cell Death Differ. 2002;9:505-12.
Puthalakath et al., The Proapoptotic Activity of the Bcl-2 Family Member Bim is Regulated by Interaction with the Dynein Motor Complex. Mol. Cell. 1999;3:287-96.
Quinsay, M. et al. Pro-Apoptotic Bnip3 Mediates Permeabilization of Mitochondria and Release of Cytrocome c via a Novel Mechanism. Circulation 118 (18), Oct. 2008: Supply 2, S388.
Raff, Social controls on cell survival and cell death. Nature. 1992;356:397-400.
Rassenti et al., ZAP-70 Compared with Immunoglobulin Heavy-Chain Gene Mutation Status as a predictor of Disease Progression in Chronic Lymphocytic Leukemia. N. Engl. J. Med. 2004;351:893-901.
Ray et al., BNIP3 Heterodimerizes with Bcl-2/Bcl-$X_L$ and Induces Cell Death Independent of a Bcl-2 Homology 3 (BH3) Domain at Both Mitochondrial and Nonmitochondrial Sites. J. Biol. Chem. 2000;275(2):1439-48.
Readhead et al., Expression of a myelin basic protein gene in transgenic shiverer mice: correction of the dysmyelinating phenotype. Cell. 1987;48:703-12.
Ren et al., BID, BIM, and PUMA Are Essential for Activation of the BAX- and BAK-Dependent Cell Death Program. Science. Dec. 2010;330:1390-3.
Riechmann et al., Reshaping human antibodies for therapy. Nature. 1988;332:323-7.
Rothbard et al., Conjugation of arginine oligomers to cyclosporine A facilitates topical delivery and inhibition of inflammation. Nature Med. 2000;6(11):1253-7.
Ryan, J. et al. BH3 profiling in whole cells by fluorimeter or FACS. Methods 61, 2013, 156-164.
Ryan et al., Heightened mitochondrial priming is the basis for apoptotic hypersensitivity of CD4+ CD8+ thymocytes. Proc Natl Acad Sci U S A. Jul. 20, 2010;107(29):12895-900. doi: 10.1073/pnas.0914878107. Epub Jul. 6, 2010.
Samson et al., A 35 amino acid fragment of leptin inhibits feeding in the rat. Endocrinology. 1996;137:5182-5.
Sattler et al., Structure of Bcl-xL-Bak Peptide Complex: Recognition Between Regulators of Apoptosis. Science. 1997;275:983-6.
Schimmer et al., Cell Death and Differentiation. 2001;8(7):725-33.
Sen, R. et al., Artemisinin triggers induction of cell-cycle arrest and apoptosis in Leishmania donovani promastigotes. J Med Microbiol. Sep. 2007;56(Pt 9):1213-8.
Sequence Search Result.
Shalaby et al., Development of humanized bispecific antibodies reactive with cytotoxic lymphocytes and tumor cells overexpressing the HER2 protooncogene. Exp. Med. 1992;175:217-25.
Shangary et al., Peptides derived from BH3 domains of Bcl-2 family members: a comparative analysis of inhibition of Bcl-2, Bcl-x(L) and Bax oligomerization, induction of cytochrome c release, and activation of cell death. Biochemistry. Jul. 30, 2002;41(30):9485-95.
Shimizu et al., Proapoptotic BH3-only Bcl-2 family members induce cytochrome c release, but not mitochondrial membrane potential loss, and do not directly modulate voltage-dependent anion channel activity. Proc Natl Acad Sci U S A. Jan. 18, 2000;97(2):577-82.
Shopes, A genetically engineered human IgG mutant with enhanced cytolytic activity. J Immunol. 1992. 148:2918-2922.
Soltow, Q. et al. Overexpression of CuZnSOD or MnSOD protects satellite cells from doxorubicin-induced apoptosis. FASEB Journal 21 (5), 2007, 577-579. Abstract only.
Song, R. et al., Carbon monoxide promotes Fas/CD95-induced apoptosis in Jurkat cells. J Biol Chem. Oct. 22, 2004;279(43):44327-34. Epub Jul. 27, 2004. Erratum in: J Biol Chem. Jun. 10, 2005;280(23):22555.
Stevenson et al., A chimeric antibody with dual Fc regions (bisFabFc) prepared by manipulations at the IgG hinge. Anti-Cancer Drug Design. 1989;3:219-30.
Strupp et al., Treatment of Cells with Detergent Activates Caspases and Induces Apoptotic Cell Death. J. Membrane Biology. Jun. 2000;175(3): 181-9.
Sugiyama, T. et al. Activation of mitochondrial voltage-dependent anion channel by a pro-apoptotic BH3-only protein Bim. Oncogene 21, 2002, 4944-4956.
Suresh et al., Bispecific Monoclonal Antibodies from Hybrid Hybridomas. Methods in Enzymology. 1986;121:210-28.
Suzuki et al., Possible Existence of Common Internalization Mechanisms among Arginine-rich Peptides. J. Biol. Chem. 2002;277:2437-43.
Terradillos et al. FEBS Lett. 2002;522(1-3):29-34.
Traunecker et al., Bispecific single chain molecules (Janusins) target cytotoxic lymphocytes on HIV infected cells. EMBO J. 1991;10:3655-9.
Tutt et al., Trispecific F(ab')3 derivatives that use cooperative signaling via the TCR/CD3 complex and CD2 to activate and redirect resting cytotoxic T cells. J. Immunol. 1991;147:60.
Vaquero, E. et al., Extracellular matrix proteins protect pancreatic cancer cells from death via mitochondrial and nonmitochondrial pathways. Gastroenterology. Oct. 2003;125(4):1188-202.
Vaux et al., Bcl-2 gene promotes haemopoietic cell survival and cooperates with c-myc to immortalize pre-B cells. Nature. 1988;335(6189):440-42.
Verhoeyen et al., Reshaping Human Antibodies: Grafting an Antilysozyme Activity. Science. 1988;239:1534-6.
Vieira et al., Cell permeable BH3-peptides overcome the cytoprotective effect of Bcl-2 and Bcl-XL. Oncogene. 2002 21:1963-77.
Vitetta et al., Redesigning Nature's Poisons to Create Anti-Tumor Reagents. Science. 1987;238:1098-104.
Vives et al., A Truncated HIV-1 Tat Protein Basic Domain Rapidly Translocates through the Plasma Membrane and Accumulates in the Cell Nucleus. J. Biol. Chem. 1997;272(25):16010-7.
Vo et al., Relative mitochondrial priming of myeloblasts and normal HSCs determines chemotherapeutic success in AML. Cell. Oct. 12, 2012;151(2):344-55.
Wang et al., Bid: A Novel BH3 Domain-Only Death Agonist. Genes Dev. 1996;10(22):2859-69.
Wang et al., Cell Permeable Bcl-2 binding Peptides: A Chemical Approach to Apoptosis Induction in Tumor Cells. Cancer Res. 2000;60:1498-502.
Wang et al., Structure based discovery of an organic compound that binds Bcl-2 protein and induces apoptosis of tumor cells. PNAS. 2000;97:7124-9.

(56) References Cited

OTHER PUBLICATIONS

Wang, The Expanding Role of Mitochondria in Apoptosis. Genes Dev. 2001;15:2922-33.
Wei et al., Proapoptotic BAX and BAK: A Requisite Gateway to Mitochondrial Dysfunction and Death. Science. 2001;292(5517):727-30.
Wei et al., tBID, a membrane-targeted death ligand, oligomerizes BAK to release cytochrome c. Genes & Development. 2000;14:2060-71.
Weinstein, Addiction to Oncogenes—the Achilles Heal of Cancer. Science. 2002;297:63-4.
Werner et al., Bcl-2 Family Member Bfl-1/A1 Sequesters Truncated Bid to Inhibit its Collaboration With Pro-Apoptotic Bak or Bax. J. Biol. Chem. 2002;277(25):22781-8.
Westerhoff et al., Magainins and the disruption of membrane-linked free-energy transduction. Proc. Natl. Acad. Sci. USA. Sep. 1989;86(17):6597-601.
Wilkinson, Immunochemical techniques inspire development of new antibody purification methods. The Scientist. 2000;14(8):25-8.
Willis et al., Apoptosis Initiated When BH3 Ligands Engage Multiple Bcl-2 Homologs, not Bax or Bak. Science. Feb. 2007;315:856-9.
Willis et al., Proapoptotic Bak is sequestered by Mcl-1 and Bcl-xL, but not Bcl-2, until displaced by BH3-only proteins. Genes Dev. 2005;19:1294-305.
Wolff et al., Monoclonal antibody homodimers: Enhanced antitumor activity in Nude Mice. Cancer Research. 1993;53:2560-5.
Wolter et al., Movement of Bax from the Cytosol to Mitochondria during Apoptosis. J. Cell Biol. 1997;139(5):1281-92.
Yamaguchi et al., Bcl-XL Protects BimEL-induced Bax Conformational Change and Cytochrome c Release Independent of Interacting with Bax or BimEL. J. Biol. Chem. 2002;277(44):41604-12.
Yang et al., Bad, a Heterodimeric Partner for Bcl-XL and Bcl-2, Displaces Bax and Promotes Cell Death. Cell. 1995;80(2):285-91.
Yang et al., Calculation of Protein Conformation from Circular Dichroism. Methods Enzymol. 1986;130:208-69.
Yasuda et al., BNIP3 α: a Human Homolog of Mitochondrial Proapoptotic protein BNIP3. Cancer Res. 1999;59:533-7.
Yi et al., Inhibition of Bid-induced apoptosis by Bcl-2. tBid insertion, Bax translocation, and Bax/Bak oligomerization suppressed. J Biol Chem. May 9, 2003;278(19):16992-9. Epub Mar. 6, 2003.
Zha et al., BH3 Domain of BAD is Required for Heterodimerization with Bcl-XL and Pro-apoptotic Activity. J. Biol. Chem. 1997;272(39):24101-4.
Zha et al., Posttranslational N-Myristoylation of BID as a Molecular Switch for targeting Mitochondria and Apoptosis. Science. 2000;290(5497)1761-5.
Zha et al., Serine Phosphorylation of Death Agonist BAD in Response to Survival Factor Results in Binding to 14-3-3 Not BCL-XL. Cell. 1996;87:619-28.
Zhou et al., Novel mutant-selective EGFR kinase inhibitors against EGFR T790M. Nature. Dec. 24, 2009;462(7276):1070-4.
Zong et al., BH3-only proteins that bind pro-survival Bcl-2 family members fail to induce apoptosis in the absence of Bax and Bak. Genes & Development. 2001;15:1481-6.
EP16787045.0, Oct. 4, 2018, Extended European Search Report.
U.S. Appl. No. 16/508,459, filed Jul. 11, 2019, Letai et al.
Pan et al., Selective BCL-2 inhibition by ABT-199 causes on-target cell death in acute myeloid leukemia. Cancer Discov. Mar. 2014;4(3):362-75. doi: 10.1158/2159-8290.CD-13/0609. Epub Dec. 17, 2013.

* cited by examiner

B

Amine Plate

Neutravidin Plate Only

Poly-L-Lysine Coated

CD19 Coated Plate

Tissue Culture Treated

HIGH THROUGHPUT BH3 PROFILING: A RAPID AND SCALABLE TECHNOLOGY TO BH3 PROFILE ON LOW NUMBERS OF CELLS

RELATED APPLICATIONS

This application is a national stage filing under 35 U.S.C. § 371 of International Application No. PCT/US2016/029495, filed Apr. 27, 2016, and entitled "HIGH THROUGHPUT BH3 PROFILING: A RAPID AND SCALABLE TECHNOLOGY TO BH3 PROFILE ON LOW NUMBERS OF CELLS" which claims the benefit under 35 U.S.C. § 119(e) of U.S. provisional application No. 62/153,475, filed Apr. 27, 2015, the contents of which are incorporated herein by reference in their entirety.

BACKGROUND OF INVENTION

Dynamic BH3 Profiling (DBP) determines how a drug alters apoptotic sensitivity of cells. The methods of dynamic BH3 profiling involved treating cells with a chemical compound in the presence of culture medium in a well for about 4-72 hours. The cells were then lifted out from the well, and separated from the culture media using a centrifuge. The separated cells were placed in BH3 profiling buffer and contacted with BH3 profiling peptides, and loss of mitochondrial membrane potential (MOMP) was measured. An increase in mitochondrial sensitivity to BH3 peptides indicated that cells are sensitive to the chemical compound. However, this is a laborious process involving a significant amount of human operator handling, thereby increasing the error rates. In addition, this process requires large quantities of limited material (e.g., tumor cells). These limitations represent a barrier to scale. Accordingly, methods of BH3 profiling that are automated, efficient and cost effective are needed.

SUMMARY OF INVENTION

In various aspects, the disclosure provides improved methods for determining how a drug alters apoptotic sensitivity of cells.

Accordingly, in some aspects, the disclosure provides a method of predicting sensitivity of cells to a test agent comprising: culturing cells on an adhesive solid surface in a culture medium having serum in the presence and absence of a test agent; contacting the cultured cells with a BH3 profiling buffer and a pro-apoptotic BH3 domain peptide (e.g., on the adhesive solid surface); measuring the amount of BH3 domain peptide induced mitochondrial outer membrane permeabilization (MOMP) in the cells; and, comparing the amount of BH3 domain peptide induced MOMP in the cells cultured in the presence of the test agent to the amount of BH3 domain peptide induced MOMP in the cells cultured in the absence of the test agent, wherein an increase in MOMP in the cells cultured in the presence of the test agent compared to the amount of BH3 domain peptide induced MOMP in the cells cultured in the absence of the test agent indicates the cells are sensitive to the test agent.

In some embodiments, the method further comprises washing the culture media from the cells prior to contacting the cells with the BH3 profiling buffer and the pro-apoptotic BH3 domain peptide.

In some embodiments, the BH3 profiling buffer is added at a concentration of 2×, 3× or 4×. In some embodiments, the BH3 profiling buffer is added at a concentration of 2× and the amount of BH3 domain peptide induced MOMP is measured by microscopy. In some embodiments, the BH3 profiling buffer is added at a concentration of 3× or 4× and the amount of BH3 domain peptide induced MOMP is measured by Fluorescence-activated cell sorting (FACS).

In some embodiments, the adhesive solid surface is coated with one or more pro-adhesive compounds. In some embodiments, the one or more pro-adhesive compounds is an extracellular matrix (ECM) protein. In some embodiments, the ECM protein is selected from the group consisting of collagen 1, laminin, collagen 4 and fibronectin. In some embodiments, the ECM protein mixture is derived from animal tissue, and is of unknown composition. In some embodiments, the one or more pro-adhesive compounds is an antibody. In some embodiments, the one or more pro-adhesive compounds is streptavidin or neutravidin.

In some embodiments, the BH3 profiling buffer is Derived from Trehalose Experimental Buffer (DTEB) or Mannitol Experimental Buffer (MEB). In some embodiments, the cells are permeabilized after, prior to, or simultaneously when contacting with the BH3 domain peptide. In some embodiments, the BH3 profiling buffer is supplemented with a permeabilizing agent. In some embodiments, the permeabilizing agent is digitonin or saponin.

In some embodiments of the method, the amount of BH3 domain peptide induced MOMP is measured by determining i) the emission of a potentiometric dye in cells that have been contacted with said potentiometric dye, or ii) the release of molecules from the mitochondrial inter-membrane space. In some embodiments, the amount of BH3 domain peptide induced MOMP is measured by FACS, plate fluorimetry, fluorescent imaging, or automated image analysis.

In some embodiments, the method further comprises fixing the cells prior to measuring MOMP. In some embodiments, the fixed cells are contacted with a potentiometric dye. In some embodiments, the potentiometric dye is 5,5',6,6'-tetrachloro-1,1',3,3'-tetraethylbenzimidazolylcarbocyanine iodide (JC-1), dihydrorhodamine 123, tetramethylrhodamine methyl ester (TMRM) or tetramethylrhodamine ethyl ester (TMRE).

In some embodiments, the fixed cells are contacted with an antibody for cytochrome C, SMAC/Diablo, Omi, adenylate kinase-2 or apoptosis-inducing factor to measure MOMP. In some embodiments, the fixed cells are contacted with an antibody for a mitochondrial antigen not released by MOMP, such as Tom20 or VDAC, e.g., as a counter-measurement of mitochondrial location after MOMP.

In some embodiments, the BH3 domain peptide is derived from the BH3 domain of a BID, a BIM, a BAD, a NOXA, a PUMA a BMF, or a HRK polypeptide.

In some embodiments, the BH3 domain peptide is selected from the group consisting of SEQ ID NO: 1-15. In some embodiments, the test agent is a therapeutic agent. In some embodiments, the test therapeutic agent is a chemotherapeutic agent.

In some embodiments, the cells are primary human tumor cells. In some embodiments, the cells are obtained from a patient derived xenograft (PDX). In some embodiments, the cells are cultured human cells. In some embodiments, the cells are primary animal tumor cells. In some embodiments, the cells are healthy cells derived from human or animal tissue. In some embodiments, the method is repeated with a plurality of test agents.

In some aspects, the disclosure provides a multi-well plate comprising a test therapeutic agent and a BH3 domain peptide, wherein each well is coated with an adhesive agent.

In some embodiments, the BH3 domain peptide is derived from the BH3 domain of a BID, a BIM, a BAD, a NOXA, a PUMA a BMF, or a HRK polypeptide. In some embodiments, the BH3 domain peptide is selected from the group consisting of SEQ ID NO: 1-15. In some embodiments, the test therapeutic agent is a chemotherapeutic agent. In some embodiments, the adhesive agent is an extracellular matrix (ECM) protein. In some embodiments, the ECM protein is selected from the group consisting of collagen 1, laminin, collagen 4 and fibronectin. In some embodiments, the adhesive agent is an antibody.

In some aspects, the disclosure provides a kit comprising a multi-well plate as described by the disclosure, and further comprising a vial containing a BH3 profiling buffer and instructions for using the kit to predict sensitivity of cells to a therapeutic agent.

BRIEF DESCRIPTION OF DRAWINGS

FIG. 5A shows a 4× image of colon tumors after dynamic BH3 Profiling. After drug treatments and BH3 Profiles, cells were stained with anti-cytochrome c and EpCam to denote mitochondria. FIG. 5B shows dose response images and curves of a colon PDX tumor. In FIG. 5B (top), cells are stained with anti-cytochrome c (shown), and also with Hoechst 33342 (not shown), and a Tom20 mitochondrial counter stain (not shown). In FIG. 5B (bottom), a dose response curve of cytochrome c loss is calculated by correlating the fluorescence intensity of Cytochrome c and Tom20.

FIG. 8A shows tumor cells (8902 cells) and other non-tumor mouse cells (Bax/Bak DKO MEFs) after a high throughput dynamic BH3 profiling (HT-DBP). The 8902 tumor cells underwent MOMP, whereas Bax/Bak DKO cells did not lose cytochrome c. The 8902 tumor cells were identified based on human EpCam staining. FIG. 8B is a quantification of FIG. 8A. FIG. 8C shows cells that were freshly isolated from a pancreatic patient derived xenograft after a HT-DBP. Pancreatic tumor cells are marked with the tumor marker EpCam, while other cells are not marked with EpCam. FIG. 8D shows a BH3 peptide dose response using HT-DBP of the pancreatic patient derived xenograft (PCA19), and of all the cells in the well (All Cells). Note that the dose response curve shifted when only the pancreatic tumor cells are analyzed.

FIG. 11A shows the response of YAPC, Panc02.03 and SU86.86 cells cultured in RPMI to 0 μM Bim peptide in 2× buffer (top) and 100 μM Bim peptide in 2× buffer (bottom). FIG. 11B shows the response of HPAC, Patu8988T and Patu8902 pancreatic cancer cells to 0 μM Bim peptide in 2× buffer (top) and 100 μM Bim peptide in 2× buffer (bottom); HPAC and Patu8988T cells were cultured in RPMI and Patu8902 cells were cultured in DMEM. FIG. 11C shows the response of BxPc3, Panc04.03 and ASPC-1 pancreatic cancer cells to 0 μM Bim peptide in 2× buffer (top) and 100 μM Bim peptide in 2× buffer (bottom); BxPc3 cells were cultured in DMEM and Panc04.03 and ASPC-1 cells were cultured in RPMI. Treatment of all pancreatic cancer cell lines shown in FIGS. 11A-11C with 100 μM Bim peptide in 2× buffer resulted in loss of cytochrome c, as measured by fluorescence microscopy.

FIG. 12A shows 8902 cells. FIG. 12B shows 8988T cells. Cells were stained with anti-cytochrome c antibody and Hoechst 33342 dyes. Data from treatment with 2×, 3×, 4× or 5× buffer concentrations are shown. Treatment of cells with 0 μM Bim peptide at 3×, 4×, and 5× resulted in non-specific loss of cytochrome c, as measured by fluorescence microscopy, indicating poor assay quality at these buffer concentrations. Peptide-induced loss of cytochrome c occurred at a concentration of 2× buffer.

FIG. 13A shows FACS data. FIG. 13B shows a histogram of FACS data. Cells were stained with anti-cytochrome c antibody. Data from treatment with 2×, 3×, 4× or 5× buffer concentrations are shown. Treatment of cells with 100 μM Bim peptide 2× and 3× concentrations of buffer resulted in peptide-induced reduction of the cytochrome c-positive cell population.

FIG. 18A shows a Bim peptide dose response at different cell numbers. FIG. 18B shows the maximum plateau of the Bim peptide dose response from FIG. 18A. FIG. 18C shows the standard deviation of the maximum plateau of the Bim dose response as a measure of assay noise. Note that while it is possible to observe dose responses at all cell numbers, based on the noise measurement from FIG. 18C, HT-DBP is optimal at 500 cells or more.

FIG. 20A shows technical replicates. FIG. 20B shows the compounds that increased apoptotic priming (on the x-axis). Cell counts are also indicated on the y-axis. FIG. 20C shows some images of compounds that did or did not increase apoptotic priming.

DETAILED DESCRIPTION OF INVENTION

Figure 1:
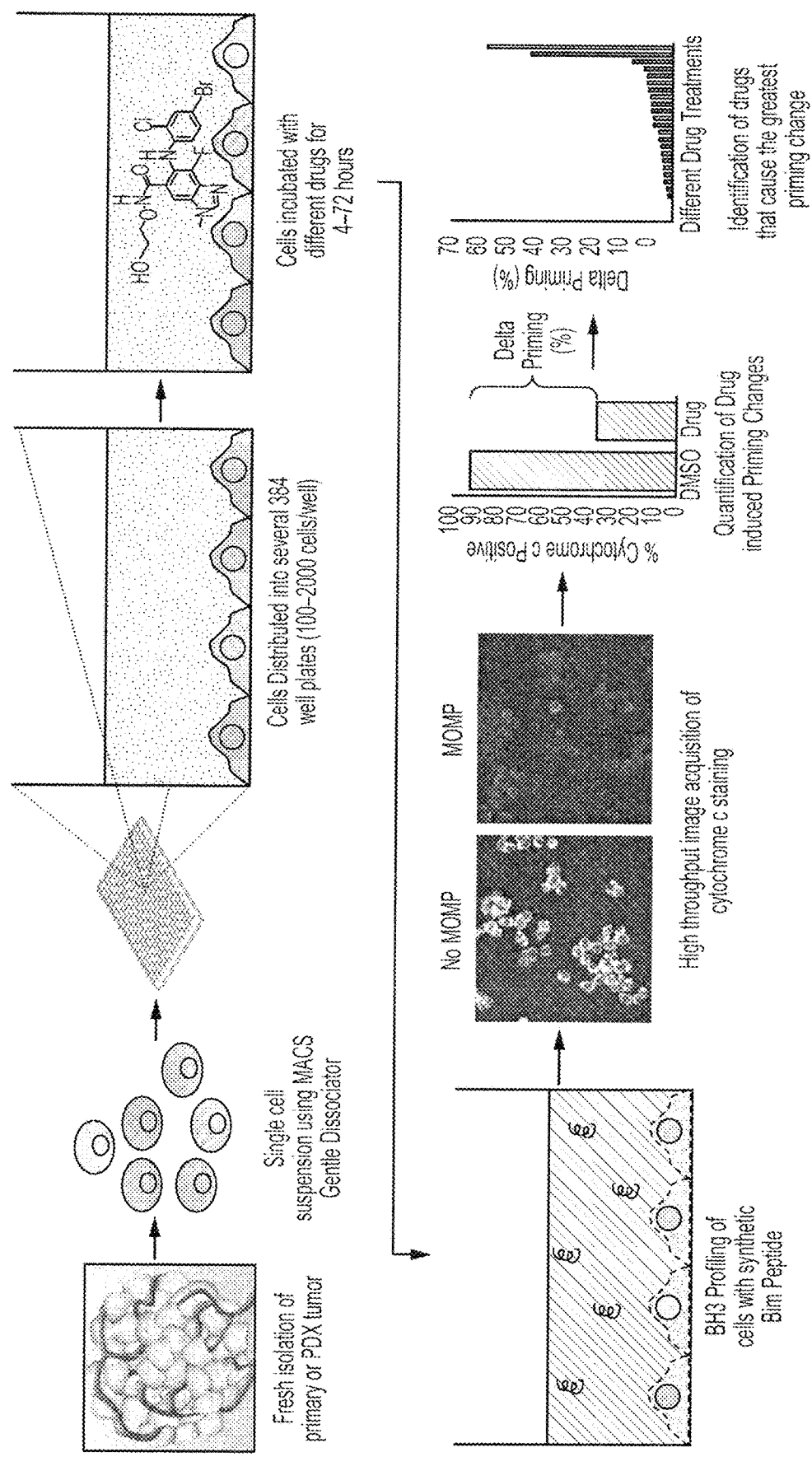
FIG. 1 shows one embodiment of a method for high throughput dynamic BH3 profiling. Tumors from patients are dissociated into single cell suspensions and distributed onto 384 well plates. Cells are treated with drug(s) for 4-72 hours and then are subjected to BH3 Profiles. The relative loss of cytochrome c (Delta Priming) indicates that this drug sensitizes cells to apoptosis and may present a compound for personalized chemotherapy or for further evaluation in a clinical setting.

Dynamic BH3 Profiling is a technique used to measure the sensitivity of cells to a test compound or therapeutic. This technique has been described previously in WO 2014/047,342, the contents of which are incorporated by reference herein. Dynamic BH3 profiling allows the identification of new drugs that move target cells closer to programmed cell death. The technique can also be used in personalized medicine since it allows identification of therapeutic drugs that are most likely to benefit the patient.

In the previously described methods of dynamic BH3 profiling, the cells were treated with the drug in the presence of culture medium, typically containing serum. After treatment with the drug, the cells were then separated from the culture medium, and washed before contacting the cells with a BH3 profiling buffer and a pro-apoptotic BH3 domain peptide. This separation step was necessary because it was expected that the presence of cell culture media, including serum, will interfere with the ability of BH3 peptides to induce mitochondrial outer membrane permeabilization. In addition, the effect of attaching cells to a surface (e.g., an assay plate) on BH3 profiles was not known, and assumed to decrease effect of peptides on cells. Thus, the previously described technique involved separating and washing the cells before exposing the cells to a pro-apoptotic BH3 domain peptide. These additional separation and washing steps made the process laborious and involved a significant amount of human operator handling, thereby increasing the risk of errors in the assay. In addition, the process required a large number of cells due to loss of material during the separation and washing steps. These limitations imposed several logistical barriers and made it difficult to scale the process into an automated or high-throughput method that could be used in personalized medicine or as a drug screening tool.

The present invention is based in part on the surprising discovery that cells do not need to be removed from a culture plate to perform dynamic BH3 profiling because the presence of cell culture media, saline solutions (e.g., PBS), and serum does not interfere with the ability of BH3 peptides to induce mitochondrial outer membrane permeabilization. Moreover, aggressive wash steps (e.g., where there is little residual volume above the cells), which often remove attached cells, are not necessary. Instead, the cells can be successively treated in the plate well with the drug and the BH3 domain peptide. This represents a critical advance over the previously described protocol of dynamic BH3 profiling. The technique can now be fully automated, and involves little human handling, which can result in operator biases and highly inconsistent data. Automation enables the use of the technique for large drug screens which was previously not possible. Also, the assay requires fewer number of cells. While the previously described technique of dynamic BH3 profiling required between 10000 and 30000 thousand cells per condition, the methods of the invention can measure signals using as few as 100 cells per well, e.g., as few as 250 cells per well. This reduction in cell numbers by at least 10 fold, e.g., at least 100, fold along with complete automation facilitates using primary human tumors, patient derived xenografts or genetically engineered animal tumor models in drug screens.

It was also discovered that dynamic BH3 profiling can be conducted under a variety of BH3 profiling buffer concentrations. Surprisingly, it was found that cells can tolerate higher concentrations of BH3 profiling (e.g., 2×-4×). This allows the method to be performed in microwell environments suitable for high throughput drug screening.

In some aspects, the disclosure provides a method of predicting sensitivity of cells to a test agent comprising: culturing cells on an adhesive solid surface in a culture medium having serum in the presence and absence of a test agent; contacting the cells with a BH3 profiling buffer and a pro-apoptotic BH3 domain peptide; measuring the amount of BH3 domain peptide induced mitochondrial outer membrane permeabilization (MOMP) in the cells; and, comparing the amount of BH3 domain peptide induced MOMP in the cells cultured in the presence of the test agent to the amount of BH3 domain peptide induced MOMP in the cells cultured in the absence of the test agent, wherein an increase in MOMP in the cells cultured in the presence of the test agent compared to the amount of BH3 domain peptide induced MOMP in the cells cultured in the absence of the test agent indicates the cells are sensitive to the test agent.

By "culturing cells in a culture medium having serum in the presence and absence of a test agent" means growing the cells in culture under suitable conditions in the presence and absence of a test agent. A "culture medium" (also referred to herein as a "cell culture medium" or "medium") is a medium for culturing cells containing nutrients that maintain cell viability and support proliferation. The disclosure contemplates various parameters and conditions for culturing the cell. The instant invention is based, in part, on the surprising discovery that the presence of cell culture media and serum do not affect the sensitivity of dynamic BH3 profiling. Therefore, in some embodiments, the cell is cultured in a culture medium having serum. The cell culture medium may contain any of the following nutrients in appropriate amounts and combination: salt(s), buffer(s), amino acids, glucose or other sugar(s), antibiotics, serum or serum replacement, and other components such as peptide growth factors, etc. Cell culture media are known in the art and may be classified as natural or artificial media. Examples of cell culture media include but are not limited to Minimum Essential Medium (MEM), Dulbecco's Modified Eagle's Medium (DMEM) and Roswell Park Memorial Institute Medium (RPMI). Selection of an appropriate medium for culturing the cell is within the capability of the skilled artisan.

Some cell lines are adherent during the wash (Colo205, HCT116, HT55), and some show significant loss during the wash. This cell loss is a known feature of washing cells with a low residual volume, and is attenuated with higher residual volumes. Previously, it was not known that BH3 profiling could be performed with residual volumes of media or wash buffer, nor the concentration of BH3 profiling buffers that could be tolerated by cells. Therefore, in some embodiments, the cell is cultured on an adhesive solid surface. This attachment facilitates quantitative analysis after BH3 profiles. In the absence of attachment, the cells are lost or are frequently moved to the edges of the well limiting quantitative analysis. In some embodiments, the solid surface is a multi-well plate. Multi-well plates can be made from plastic (e.g., polystyrene) or glass. Generally multi-well plates comprise an array of 96, 384 or 1536 wells. In some embodiments, the solid surface is treated to favor the adherence of the cells to the surface. In some embodiments, the surface is treated by corona discharge. Alternatively, the surface may be treated with a pro-adhesive compound. Pro-adhesive compounds include but are not limited to poly-D-lysine, polyethyleneimine (PEI), Wheat germ agglutinin (WGA) and Extracellular Matrix Proteins (e.g., collagen 1, laminin, collagen 4 and fibronectin). Other non-cancer cells, which themselves secrete extracellular matrix proteins, can also be cultured on the surface alongside the cancer cells. In some embodiments, the pro-adhesive compound is an antibody for a cell surface protein. For example, an antibody specific for a cancer cell surface protein (such as EpCam, CD19, CD45) may be coated onto the surface and upon addition of a cancer cell, adhere the cancer cell to the surface. In some embodiments, the pro-adhesive compound is streptavidin and the cell is biotinylated.

The cells are cultured in the culture medium under suitable conditions and a time sufficient to permit the test agent from moving the cells closer to programmed cell death. In some embodiments, the cells are cultured in the form of organoids. Any number of cells suitable for generating a BH3 profile can be used. The number of cells can be expressed as the number of cells per well of a culture plate. In some embodiments, the number of cells ranges between about 100 cells per well to about 10000 cells per well. In some embodiments, the number of cells ranges between about 100 cells per well to about 500 cells per well. In some embodiments, the number of cells ranges between about 200 cells per well to about 10000 cells per well. In some embodiments, the number of cells ranges from about 250 cells per well to about 500 cells per well. In some embodiments, the number of cells ranges from about 300 cells per well to about 750 cells per well. In some embodiments, the number of cells ranges from about 400 cells per well to about 600 cells per well. In some embodiments, the number of cells is about 100, about 150, about 200, about 250, about 300, about 350, about 400, about 450, or about 500 cells per well. Suitable conditions include growing the cell under standard cell culture conditions in a cell culture incubator (e.g., at 37° C. in a humidified atmosphere of >80% relative humidity air and 5 to 10% $CO_2$). In some embodiments, the cells are cultured in the presence or absence of the test agent for at least 30 minutes, 45 minutes, 1 hour, 2 hours, 4 hours, 8 hours, 12 hours, 16 hours, 20 hours, 1 day, at least 2 days, at least 3 days, or at least 4 days.

Cell sensitivity to the test agent is determined by contacting the cells or cellular component (e.g., mitochondria) with a BH3 profiling buffer and a BH3 domain peptide from the pro-apoptotic BCL-2 family or small molecules with direct mitochondrial activity. This includes, but is not limited to ABT-199, ABT-263, ABT-737, WEHI-539, A-1210477, and ABT-199. The ability of BH3 peptides to induce mitochondrial outer membrane permeabilization (MOMP) is measured in the cells (or cellular component, e.g., mitochondria) exposed to the test agent and the control cells (or cellular component, e.g., mitochondria) not exposed to the test agent. An increase in BH3 peptide-induced MOMP in the cells cultured in the presence of the test agent compared to the amount of BH3 domain peptide induced MOMP in the cells cultured in the absence of the test agent indicates that the cells are responsive (e.g., cell death will be induced) to the test agent. No change in MOMP in the cells cultured in the presence of the test agent compared to the amount of BH3 domain peptide induced MOMP in the cells cultured in the absence of the test agent indicates that the drug has no effect on inducing cell death. A decrease in MOMP in the cells cultured in the presence of the test agent compared to the amount of BH3 domain peptide induced MOMP in the cells cultured in the absence of the test agent indicates that the test agent has a desensitizing or protective effect on the cells. Test agents that have a desensitizing or protective effect with respect to BH3 domain peptide-induced cell death are potentially useful agents for treating other non-cancer diseases (e.g., neurodegenerative diseases), or as co-therapies to protect different cell types from chemotherapy-induced toxicity.

The difference in the level of BH3 peptide-induced MOMP of cells that have been exposed to the test agent as compared to the level of BH3 peptide-induced MOMP of cells that have not been exposed to the test agent is statistically significant. By statistically significant is meant that the alteration is greater than what might be expected to happen by chance alone. Significant differences may be identified by using an appropriate statistical test. Tests for statistical significance are well known in the art and are exemplified in Applied Statistics for Engineers and Scientists by Petruccelli, Chen and Nandram 1999 Reprint Ed. As used here, the term "BH3 Profiling Buffer" refers to an aqueous solution comprising a sugar, a pH buffer, salts, chelators and a carbon source for the electron transport chain that is useful for performing measurements of MOMP. In some embodiments, the BH3 Profiling Buffer is a Derived from Trehalose Experimental Buffer (DTEB). In some embodiments, the BH3 Profiling Buffer is a Mannitol Experimental Buffer (MEB). DTEB is comprised of 135 mM trehalose, 10 mM Hepes, 50 mM KCl, 20 µM EGTA, 20 µM EDTA, 0.1% BSA and 5 mM Succinate. MEB is comprised of 150 mM mannitol, 10 mM Hepes, 50 mM KCl, 20 µM EGTA, 20 µM EDTA, 0.1% BSA and 5 mM Succinate. Sucrose and other sugars may be used in the place of mannitol. Some increases in KCl are tolerated, however can be detrimental to BH3 profiling. Concentrated buffers (2×-5×) involve proportionally increasing the concentration of the above reagents as described in Table 1 below.

TABLE 1

Composition of Mannitol Experimental Buffer (MEB)

|  | 1X | 2X | 3X | 4X | 5X |
|---|---|---|---|---|---|
| Mannitol | 150 mM | 300 mM | 450 mM | 600 mM | 750 mM |
| HEPES-KOH | 10 mM | 20 mM | 30 mM | 40 mM | 50 mM |
| KCl | 50 mM | 100 mM | 150 mM | 200 mM | 250 mM |
| EGTA | 0.02 mM | 0.04 mM | 0.06 mM | 0.08 mM | 0.1 mM |
| EDTA | 0.02 mM | 0.04 mM | 0.06 mM | 0.08 mM | 0.1 mM |
| BSA | 0.10% | 0.20% | 0.30% | 0.40% | 0.50% |
| Succinate | 5 mM | 10 mM | 15 mM | 20 mM | 25 mM |

Without wishing to be bound by any particular theory, increased buffer concentration (for example 2×-5× buffer) enables BH3 profiling to be conducted in the presence of media having serum. In some embodiments, the buffer concentration ranges from about 1× to about 5×. In some embodiments, the buffer concentration ranges from about 1× to 4×. In some embodiments, the buffer concentration ranges from about 2× to about 3×. In some embodiments, the buffer concentration is about 1×, about 2× about 3×, about 4×, or about 5×. In some embodiments, the buffer concentration is 1×, 2×, 3×, 4×, or 5×.

Pro-apoptotic BCL-2 BH3 proteins and peptides include: Bcl-2 interacting mediator of cell death (BIM); a mutant thereof (BIM AV); BH3 interacting domain death agonist (BID); Bcl-2-associated death promoter (BAD); NOXA; p53 up-regulated modulator of apoptosis (PUMA); Bcl-2-modifying factor (BMF) and harakiri (HRK) (See, Table 2).

In some embodiments, the method comprises permeabilizing the cell after, prior to, or simultaneously when contacting with the BH3 domain peptide. Generally, permeabilization refers to the process of treating a cell with a reagent such that the cell membrane becomes permeable without permeabilizing the mitochondrial outer membrane. Reagents used for permeabilization include organic solvents (e.g., acetone and methanol) and detergents (e.g., digitonin, saponin, Triton X-100 and Tween-20). Without wishing to be bound by any particular theory, the cell is permeabilized to permit the BH3 peptides access to the mitochondria. Cells are permeabilized by methods known in the art. For example, the cell are permeabilized by contacting the cell with digitonin, saponin, methanol, Triton X-100 or other art-recognized cell-permeabilization agents. In some embodiments, the BH3 profiling buffer comprises the permeabilizing reagent, such as digitonin or saponin.

The skilled artisan recognizes several methods for adding the test agent, BH3 profiling buffer and/or BH3 domain peptide to the cultured cells. For example, automated liquid handling systems are generally utilized for high throughput drug screening. Automated liquid handling systems utilize arrays of liquid dispensing vessels, controlled by a robotic arm, to distribute fixed volumes of liquid to the wells of an assay plate. Generally, the arrays comprise 96, 384 or 1536 liquid dispensing tips. Non-limiting examples of automated liquid handling systems include digital dispensers (e.g., HP D300 Digital Dispenser) and pinning machines (e.g., MULTI-BLOT™ Replicator System, CyBio, Perkin Elmer Janus). Non-automated methods are also contemplated by the disclosure, and include but are not limited to a manual digital repeat multichannel pipette.

After the cells are treated with the BH3 domain peptide, the mitochondrial outer membrane permeabilization (MOMP) is measured. Outer membrane permeabilization can be measured in several ways. For example, outer membrane permeabilization can be measured by determining the loss of mitochondrial membrane potential. Loss of mitochondrial membrane potential is measured by, for example, treating the cells with a potentiometric or radiometric dye. Examples of potentiometric dyes include, but are not limited to, the fluorescent JC-1 probe (5,5',6,6'-tetrachloro-1,1',3,3'-tetraethylbenzimidazolylcarbocyanine iodide) or dihydrorhodamine 123, or tetramethylrhodamine methyl ester (TMRM) or tetramethylrhodamine ethyl ester (TMRE). These and other potentiometric dyes are well-known in the art.

Alternatively, outer membrane permeabilization is determined by measuring the release of molecules from the mitochondrial inter-membrane space. Examples of molecules released from the mitochondrial inter-membrane space include cytochrome c, SMAC/Diablo, Omi, adenylate kinase-2 or apoptotic-inducing factor (AIF). The release of molecules from the mitochondrial inter-membrane space can be measured by methods well-known in the art. For example, the release of the molecules can be measured by using antibodies to the molecules, i.e., antibodies to cytochrome c, SMAC/Diablo, Omi, adenylate kinase-2 or apoptotic-inducing factor (AIF). Detection can be for example, by ELISA, FACS, immunoblot, immunofluorescence, immunohistochemistry, plate fluorimetry, fluorescent imaging or automated image analysis. Analysis of the cells can be manually accomplished using a microscope or automated for example by using software such as CellProfiler or Metamorph image analysis software to locate nuclei.

Optionally, the cells are fixed prior to measuring outer membrane permeabilization. Cells are fixed by methods known in the art, such as by using an aldehyde (e.g., formaldehyde), or methanol.

Mitochondrial outer membrane permeabilization can be measured at the single cell level or multi-cell level. Additionally, some of the methods disclosed herein allow for subpopulations of cells to be assayed. For example, a tumor-specific or tumor-associated marker (e.g., EpCam) can be used to identify tumor cells. This allows for the ability to discriminate between normal and tumor cells. MOMP is then measured as described herein in the tumor cells.

In some embodiments, the cells used in the methods described herein are cancer cells or cells that are suspected of being cancerous. In some embodiments, the cells comprise an immortalized cancer cell line. In some embodiments, the cells are immortalized mouse or human cancer cell lines. In some embodiments, the cells are non-malignant human or mouse primary cells. Established cancer cell lines are well-known in the art and include for example pancreatic cancer cell lines (e.g., YAPC, Panc02.03 and SU86.86, etc.), breast cancer cell lines (e.g., AU565, BT-20, CAL-120, HMEL and KPL-1, etc.), kidney cancer lines (e.g., 769-P, ACNH, HEK TE, SLR 20 and UMRC2, etc.), bone cancer cell lines (e.g., CAL-78, HOS, MG-63 and SK-ES-1, etc.) and lymphoid cancer cell lines (e.g., AML-193, BDCM, CML-T1 and JM1, etc.). The skilled artisan recognizes other cancer cell lines, for example those disclosed in Barretina et al. (The Cancer Cell Line Encyclopedia enables predictive modelling of anticancer drug sensitivity. Nature. 2012 Mar. 28; 483(7391):603-7. doi: 10.1038/nature11003). In some embodiments, the cells are derived from a subject. For example, a cancer cells cell may be isolated from a subject by a surgical technique (e.g., biopsy). Thus, in some embodiments, the cells are primary tumor cells, e.g., primary human tumor cells. In some embodiments, the cells are cultured human cells. In some embodiments, the cells are primary animal tumor cells. In some embodiments, the cells comprise a patient-derived xenograft (PDX). As used herein, the term "patient-derived xenograft" (PDX) refers to tissue generated by the implantation of cancerous primary tumor into an immunodeficient mouse.

In methods including culturing cells on an adhesive solid surface, non-cancerous cells can also be used. In some embodiments, the non-cancerous cells are normal healthy cells (e.g., cells that do not have any patent or latent pathological condition). In some embodiments, the non-cancerous cells are infected with an infectious agent, e.g., a virus or an intracellular bacterium. In some embodiments, the non-cancerous cells are from an organ that is otherwise not functioning normally. In some embodiments, the non-cancerous cells are subject to stress, e.g., vascular stress such as hypoxia, stroke, myocardial infarction, among others. In some embodiments, the cells are healthy cells derived from human or animal tissue. For example, non-cancerous cells can be used in a BH3 Profiling assay provided herein, e.g., an assay involving culturing cells on an adhesive solid surface in a culture medium having serum, to identify agents exhibiting a protective effect against BH3 domain peptide-induced cell death; such agents may be useful for lowering cell death priming during neurodegenerative disease. In another embodiment, a mouse may be treated with a particular agent and then sacrificed. High throughput BH3 profiling according to the present disclosure, e.g., involving culturing cells on an adhesive solid surface, may be performed on the tissues of the mouse to identify if the agent has toxic effects. Alternatively, high throughput BH3 profiling according to the present disclosure, e.g., involving culturing cells on an adhesive solid surface, may be carried out on a panel of normal cells to perform toxicity screens of drugs on normal primary tissues. BH3 profiling according to the present disclosure, e.g., involving culturing cells on an adhesive solid surface, of normal cells may also be useful to test for the presence of toxic agents (e.g., radiation, gas, biological agents, etc.) in an environment.

As used herein, "a subject" is preferably a mammal. The mammal is, for example, a human, non-human primate, mouse, rat, dog, cat, horse, or cow. In some embodiments, the subject is a genetically-modified animal. For example, a mouse can be genetically engineered to develop a particular cancer. In some embodiments, the subject has been previously diagnosed as having cancer, and possibly has already undergone treatment for cancer. Alternatively, in some embodiments, the subject has not been previously diagnosed as having cancer.

Exemplary test agents in accordance with the present disclosure include, but are not limited to small organic molecules, small inorganic molecules, peptides, proteins, protein analogs, enzymes, nucleic acids, nucleic acid analogs, antibodies, antigens, hormones, lipids, polysaccharides, growth factors, viruses, cells, bioactive agents, pharmaceutical agents, and combinations and prodrugs thereof. In some embodiments, a test agent is an anticancer agent, such as, a chemotherapeutic agent. Further exemplary test agents include, but are not limited to, gases, fine particles, radiation, electromagnetic radiation, and aerosols.

Examples of small molecule chemotherapeutic agents include alkylating agents (cyclophosphamide, chlormethine, temozolomide), anthracyclines (daunorubicin, doxorubicin, mitoxantrone), taxanes (paclitaxel, docetaxel), histone deacetylase inhibitors (vorinostat, romidepsin), topoisomerase I/II inhibitors (irinotecan, topotecan, etoposide), kinase inhibitors (gefitinib, imatinib, bortezomib), nucleotide analogs and precursor analogs (azacitidine, fluorouracil, methotrexate), platinum-based agents (cisplatin, carboplatin), retinoids (alitretinoin, bexarotene) and vinca alkaloids (vinblastine, vindesine, vinorelbine). Examples of peptides and proteins include bleomycin, dactinomycin, antitumor antibodies (anti-HER2/neu, alemtuzumab, trastuzumab, brentuximab). The skilled artisan recognizes chemotherapeutic RNAi molecules as RNAi molecules that target expression of genes related to cancer. For example, RNAi molecules directed against HoxA1 can inhibit mammary tumor cell formation, as disclosed by Brock et al. Sci Transl Med 6: 217ra2 (2014). In some embodiments, chemotherapeutic agents include, but are not limited to, kinase inhibitors, apoptosis inducers, angiogenesis inhibitors, and monoclonal antibodies.

In some aspects, the disclosure relates to personalized medicine. In some embodiments, methods described herein are useful for the customization of chemotherapeutic regimens. For example, high throughput BH3 profiling can be performed on cancer cells isolated from a subject having cancer in order to determine the cancer's sensitivity to a panel of known chemotherapeutic agents. Chemotherapeutic agents include but are not limited to kinase inhibitors, apoptosis inducers, angiogenesis inhibitors and monoclonal antibodies.

In some aspects, the disclosure relates to drug discovery. In some embodiments, methods described by the disclosure are useful for screening large libraries of test agents to identify new drugs that move cells closer to programmed cell death.

Pro-Apoptotic BCL-2 BH3 Domain Peptides

Pro-Apoptotic BCL-2 BH3 domain peptides have been described previously in WO 2014/047,342, the contents of which are incorporated by reference herein. In particular, a Pro-apoptotic BCL-2 BH3 domain peptide is less than 195 amino acids in length, e.g., less than or equal to 150, 100, 75, 50, 35, 25 or 15 amino acid in length. Non-limiting examples of pro-apoptotic BCL-2 BH3 peptides include: Bcl-2 interacting mediator of cell death (BIM); a mutant thereof (BIM AV); BH3 interacting domain death agonist (BID); Bcl-2-associated death promoter (BAD); NOXA; p53 up-regulated modulator of apoptosis (PUMA); Bcl-2-modifying factor (BMF) and harakiri (HRK).

In some embodiments, a pro-apoptotic BCL-2 BH3 domain peptide includes the sequence of SEQ ID NO: 1-15 shown in Table 2. PUMA2A (SEQ ID NO: 16) is a negative control peptide.

TABLE 2

Pro-Apoptotic

| Peptide | Sequence | SEQ ID NO: |
|---|---|---|
| BIM | Ac-MRPEIWIAQELRRIGDEFNA-NH2 | 1 |
| BIM AC | AC-MRPEIWIAQELRRIGDEFNV-NH2 | 2 |
| BID | EDIIRNIARHLAQVGDSMDR | 3 |
| BIM AV | MRPEIWIAQELRRIGDEFNA | 4 |
| BID mut | EDIIRNIARHAAQVGASMDR | 5 |
| BAD | LWAAQRYGRELRRMSDEFEGSFKGL | 6 |
| BIK | MEGSDALALRLACIGDEMDV | 7 |
| NOXA A | AELPPEFAAQLRKIGDKVYC | 8 |
| NOXA B | PADLKDECAQLRRIGDKVNL | 9 |
| HRK S S | AAQLTAARLKALGDELHQ | 10 |
| PUMA | EQWAREIGAQLRRMADDLNA | 11 |
| BMF | HQAEVQIARKLQLIADQFHR | 12 |
| huB AD | NLWAAQRYGRELRRMSDEFVDSFKK | 13 |
| BAD mut | LWAAQRYGREARRMSDEFEGSFKGL | 14 |
| MS1 | RPEIWMTQGLRRLGDEINAYYAR | 15 |
| PUMA2A | EQWAREIGAQARRMAADLNA | 16 |

In some embodiments, a BH3 domain peptide include a peptide which includes (in whole or in part) the sequence NH$_2$-XXXXXXXXXXLXXXXDXXXX-COOH (SEQ ID NO: 17). As used herein X may be any amino acid. Alternatively, the BH3 domain peptides include at least 5, 6, 7, 8, 9, 15 or more amino acids of SEQ ID NO: 17.

The BH3 domain peptides can be modified using standard modifications. Modifications may occur at the amino (N-), carboxy (C-) terminus, internally or a combination of any of the preceding. In one aspect described herein, there may be more than one type of modification on the polypeptide. Modifications include but are not limited to: acetylation, amidation, biotinylation, cinnamoylation, farnesylation, formylation, myristoylation, palmitoylation, phosphorylation (Ser, Tyr or Thr), stearoylation, succinylation, sulfurylation and cyclisation (via disulfide bridges or amide cyclisation), and modification by Cys3 or Cys5. The modified BH3 domain peptides retain the biological activity of BH3 domain peptides. By retaining the biological activity, it is meant that cell death is induced by the BH3 polypeptide, although not necessarily at the same level of potency as that of the naturally-occurring BH3 domain polypeptide. The terms induced and stimulated are used interchangeably throughout the specification.

Optionally, the BH3 domain peptide is attached to a transduction domain. A transduction domain directs a peptide in which it is present to a desired cellular destination. Thus, the transduction domain can direct the peptide across the plasma membrane, e.g., from outside the cell, through the plasma membrane, and into the cytoplasm. Alternatively, or in addition, the transduction domain can direct the peptide to a desired location within the cell, e.g., the nucleus, the ribosome, the ER, mitochondria, a lysosome, or peroxisome. In some embodiments, the transduction domain is derived from a known membrane-translocating sequence. Alternatively, transduction domain is a compound that is known to facilitate membrane uptake such as polyethylene glycol, cholesterol moieties, octanoic acid and decanoic acid. The transduction domain may be linked either to the N-terminal or the C-terminal end of BH3 domain peptide.

The BH3 domain peptides and/or the transduction domain peptides can be polymers of L-amino acids, D-amino acids, or a combination of both. Alternatively, the BH3 domain peptides and/or the transduction domain peptides are cyclic peptides. Cyclic peptides are prepared by methods known in the art. For example, macrocyclization is often accomplished by forming an amide bond between the peptide N- and C-termini, between a side chain and the N- or C-terminus [e.g., with K3Fe(CN)6 at pH 8.5] (Samson et al., Endocrinology, 137: 5182-5185 (1996)), or between two amino acid side chains. See, e.g., DeGrado, Adv Protein Chem, 39: 51-124 (1988).

BH3 domain peptides and/or the transduction domain peptides are prepared using modern cloning techniques, or may be synthesized by solid state methods or by site-directed mutagenesis. In some embodiments, native BH3 domain peptides and/or transduction domain peptides can be isolated from cells or tissue sources by an appropriate purification scheme using standard protein purification techniques. In another embodiment, BH3 domain polypeptides and/or transduction domain peptides are produced by recombinant DNA techniques. Alternative to recombinant expression, BH3 domain peptides and/or transduction domain peptides can be synthesized chemically using standard peptide synthesis techniques.

In various embodiments, the BH3 peptide maintains its secondary structure, e.g., α-helical structure. Methods of helix stabilization are known in the art.

An "isolated" or "purified" BH3 domain peptide is substantially free of cellular material or other contaminating proteins from the cell or tissue source from which the BH3 domain peptide is derived, or substantially free from chemical precursors or other chemicals when chemically synthesized.

Multi-Well Plates

In some aspects, the disclosure provides a multi-well cell culture plate comprising a test therapeutic agent and a BH3 domain peptide, wherein each well is coated with an adhesive agent. In some embodiments, the multi-well plate is plastic or glass. In some embodiments, the multi-well plate comprises an array of 6, 24, 96, 384 or 1536 wells. However, the skilled artisan recognizes that multi-well plates may be constructed into a variety of other acceptable configurations, such as a multi-well plate having a number of wells that is a multiple of 6, 24, 96, 384 or 1536. For example, in some embodiments, the multi-well plate comprises an array of 3072 wells (which is a multiple of 1536).

In some embodiments, each well of the plate is coated with an adhesive agent. In some embodiments, the adhesive agent is poly-D-lysine, polyethyleneimine (PEI), or Wheat germ agglutinin (WGA). In some embodiments, the adhesive agent is Extracellular Matrix (ECM) Protein. In some embodiments, the ECM protein is selected from the group consisting of collagen 1, laminin, collagen 4 and fibronectin. In some embodiments, the adhesive agent is an combination of ECM proteins (e.g., Matrigel, or one or more ECM proteins secreted by feeder cells). In some embodiments, the adhesive agent is an antibody. For example, an antibody against a cell surface protein may be coated onto each well of the multi-well plate. In some embodiments, the adhesive agent is streptavidin.

As used herein, the term "test therapeutic agent" refers to a molecule, peptide, protein, or compound or combination thereof that is being assessed to determine its therapeutic value with respect to a particular disease. For example, the ability of a new monoclonal antibody may be tested for the ability to induce apoptosis in tumor cells. In some embodiments, the plate comprises a test therapeutic agent. In some embodiments, the test therapeutic agent is a chemotherapeutic agent. In some embodiments, the plate comprises more than one test therapeutic agent. For example, the plate may be used to test a panel of chemotherapeutic agents, each agent either alone or in combination with another agent(s). In some embodiments, each well of the plate comprises a single test therapeutic agent. In some embodiments, each well of the plate comprises at least 2, at least 3, at least 4, at least 5, at least 6, at least 7, at least 8, at least 9 or at least 10 therapeutic agents. In some embodiments, each well of the plate comprises more than 10 therapeutic agents.

Non-limiting examples of chemotherapeutic agents include small molecules, peptides or proteins (e.g., peptide antibiotics and antibodies) and RNA-interference (RNAi) molecules. Examples of small molecule chemotherapeutic agents include alkylating agents (cyclophosphamide, chlormethine, temozolomide), anthracyclines (daunorubicin, doxorubicin, mitoxantrone), taxanes (paclitaxel, docetaxel), histone deacetylase inhibitors (vorinostat, romidepsin), topoisomerase I/II inhibitors (irinotecan, topotecan, etoposide), kinase inhibitors (gefitinib, imatinib, bortezomib), nucleotide analogs and precursor analogs (azacitidine, fluorouracil, methotrexate), platinum-based agents (cisplatin, carboplatin), retinoids (alitretinoin, bexarotene) and vinca alkaloids (vinblastine, vindesine, vinorelbine). Examples of peptides and proteins include bleomycin, dactinomycin, antitumor antibodies (anti-HER2/neu, alemtuzumab, trastuzumab, brentuximab). The skilled artisan recognizes chemotherapeutic RNAi molecules as RNAi molecules that target expression of genes related to cancer. For example, RNAi molecules directed against HoxA1 can inhibit mammary tumor cell formation, as disclosed by Brock et al. Sci Transl Med 6: 217ra2 (2014).

In some embodiments, the multi-well plate comprises a BH3 domain peptide. In some embodiments, the BH3 domain peptide is derived from the BH3 domain of a BID, a BIM, a BAD, a NOXA, a PUMA a BMF, or a HRK polypeptide. In some embodiments, the BH3 domain peptide is selected from the group consisting of SEQ ID NO: 1-15. In some embodiments, the plate comprises more than one BH3 domain peptide. For example, in some embodiments, a plate comprises at least 2, at least 3, at least 4, at least 5, at least 6, at least 7, at least 8, at least 9 or at least 10 BH3 domain peptides.

Kits

Some aspects of the invention include kits for performing BH3 Profiling. In some embodiments, the kit comprises a multi-well plate having a test therapeutic agent and a BH3 domain peptide. In some embodiments, each well of the multi-well plate is coated with an adhesive agent. In some embodiments, the adhesive agent is an ECM protein. In some embodiments, the ECM protein is selected from the group consisting of collagen 1, laminin, collagen 4 and fibronectin. In some embodiments, the adhesive agent is an antibody. For example, an antibody against a cell surface protein may be coated onto each well of the multi-well plate. In some embodiments, the adhesive agent is streptavidin.

In some embodiments, the kit comprises a multi-well plate having a test therapeutic agent. In some embodiments, the test therapeutic agent is a chemotherapeutic agent. In some embodiments, the kit comprises a multi-well plate having at least 2, at least 3, at least 4, at least 5, at least 6, at least 7, at least 8, at least 9 or at least 10 therapeutic agents. In some embodiments, the kit comprises a multi-well plate, wherein each well of the plate comprises more than 10 therapeutic agents. In some embodiments, the kit comprises a multi-well plate having a BH3 domain peptide. In some embodiments, the BH3 domain peptide is derived from the BH3 domain of a BID, a BIM, a BAD, a NOXA, a PUMA a BMF, or a HRK polypeptide. In some embodiments, the BH3 domain peptide is selected from the group consisting of SEQ ID NO: 1-15.

In some aspects, the kit further comprises a vial containing a BH3 profiling buffer. In some embodiments, the vial is a glass or plastic vial. In some embodiments, the vial comprises volumetric markings on its surface. In some embodiments, the BH3 profiling buffer is at a concentration of 1×, 2×, 3×, 4×, 5×, 6×, 7×, 8×, 9×, or 10×. In some embodiments, the BH3 profiling buffer is at a concentration above 10×. In some embodiments, the BH3 profiling buffer is Derived from Trehalose Experimental Buffer (DTEB) or Mannitol Experimental Buffer (MEB). In some embodiments, the BH3 profiling buffer is supplemented with a permeabilizing agent. In some embodiments, the permeabilizing agent is digitonin or saponin.

In some embodiments, the kit further comprises a potentiometric dye. In some embodiments, the potentiometric dye is 5,5',6,6'-tetrachloro-1,1',3,3'-tetraethylbenzimidazolylcarbocyanine iodide (JC-1), dihydrorhodamine 123, tetramethylrhodamine methyl ester (TMRM) or tetramethylrhodamine ethyl ester (TMRE). Alternatively, in some embodiments, the kit further comprises an antibody for cytochrome c, SMAC/Diablo, Omi, adenylate kinase-2 or apoptosis-inducing factor.

In some aspects, the kit further comprises instructions for using the kit to predict the sensitivity of cells to a therapeutic agent. Instructions are generally provided as a printed pamphlet or paper sheet but may also include any oral or electronic instructions provided in any manner such that a user will clearly recognize that the instructions are to be associated with the kit, for example, audiovisual (e.g., videotape, DVD, etc.), Internet, and/or web-based communications, etc.

The invention will be further illustrated in the following non-limiting examples.

EXAMPLES

Example 1: High Throughput Dynamic BH3 Profiling

Dynamic BH3 Profiling (DBP) determines how a drug alters apoptotic sensitivity of primary human tumors (or patient derived xenografts). Currently used methods of dynamic BH3 profiling involve treating cells with a chemical compound in a well for 16-24 hours, lifting the cells off the well, using a centrifuge to separate cells from media and placing them in a BH3 profiling buffer (DTEB) and BH3 profiling peptides. Loss of endogenous cytochrome c is measured, and instances where there is significant loss indicates that a drug sensitizes cells for apoptosis. This is a laborious process involving a lot of human operator handling and a lot of tumor cells both which represent a barrier to scale.

This example describes an embodiment of high throughput BH3 Profiling protocol in which the cells are not removed from culture and the drugs, BH3 profile buffers and peptides are added to the cells in situ. There are two critical differences between the protocol described here and currently used dynamic BH3 profiling protocols. First, this protocol is fully automated, and involves little human handling once tumors have been processed into single cells. Automation enables undertaking large chemical screens. Furthermore, human handling may result in operator biases resulting in highly inconsistent data. Second, the assay requires fewer numbers of cells to perform a dynamic BH3 profile compared to currently used methods. While other methods require between 10000 and 30000 thousand cells per condition, the instant protocol allows measurement of signals using as few as 250 cells per well or fewer. This reduction in cell numbers by at least 10-fold, along with complete automation, facilitates using primary human tumors or patient derived xenografts (PDX) in chemical screens. In sum, the two valuable outputs of this technology are: (1) high throughput chemical discovery of apoptosis sensitizers on primary human tumors or Patient Derived Xenografts (PDX) and (2) enabling personalization of chemotherapy using multiple drugs and combinations of drugs. An embodiments of the protocol is described below and in FIG. 1.

Protocol:
1. Tumors are made into single cell suspensions (by mechanical lysis and enzymatic digestion).
2. Cells are plated into multi-well plates coated with a pro-adhesive compound (e.g., collagen or an antibody targeting a cell surface marker of tumor cells). Chemicals are pinned into the plate using a pinning machine. Cells are incubated with compound for a period of 4 to 72 hours.
3. Optionally a pre-BH3 profile is performed to identify a single peptide concentration to perform the remainder of the assay. This pre-BH3 profile is performed on wells without compounds, and is performed at least 4 hours prior to the BH3 profile on the compound treated cells.
4. Optionally, culture media is washed out using an automated plate washer, and DTEB or another BH3 profiling buffer (e.g., Mannitol Experimental Buffer) is washed in. Alternatively, a saline solution such as PBS is washed into the well, and a 2× buffer is added to the cells without removal of the saline solution. A 2× buffer may be added to cells without the removal of media.
5. BH3 peptides are printed or pinned into the wells. Alternatively, cells are washed with a saline solution, peptides are printed into wells, and the 2× buffer is subsequently added. Alternatively, the 2× buffer is added with BH3 peptides.
6. Formaldehyde buffer added to fix cells using a multi-well dispenser.
7. Neutralizing buffer added to stop formaldehyde activity.
8. Staining solutions added to stain cytochrome c.
9. Optionally, staining solution is washed out to reduce background signal.
10. Quantified loss of cytochrome c using fluorescence microscopy or FACS and image analysis software (e.g., Metamorph Image Analysis)

Results

This method is almost a fully automated procedure with little human handling required once the cells are in single cell suspension (FIG. 1). It has been applied to several cancer cell lines (FIG. 3, 4, 11) several PDX models (FIG. 5), primary tumors (FIG. 6), and genetically engineered mouse models (FIG. 7).

Figure 3:
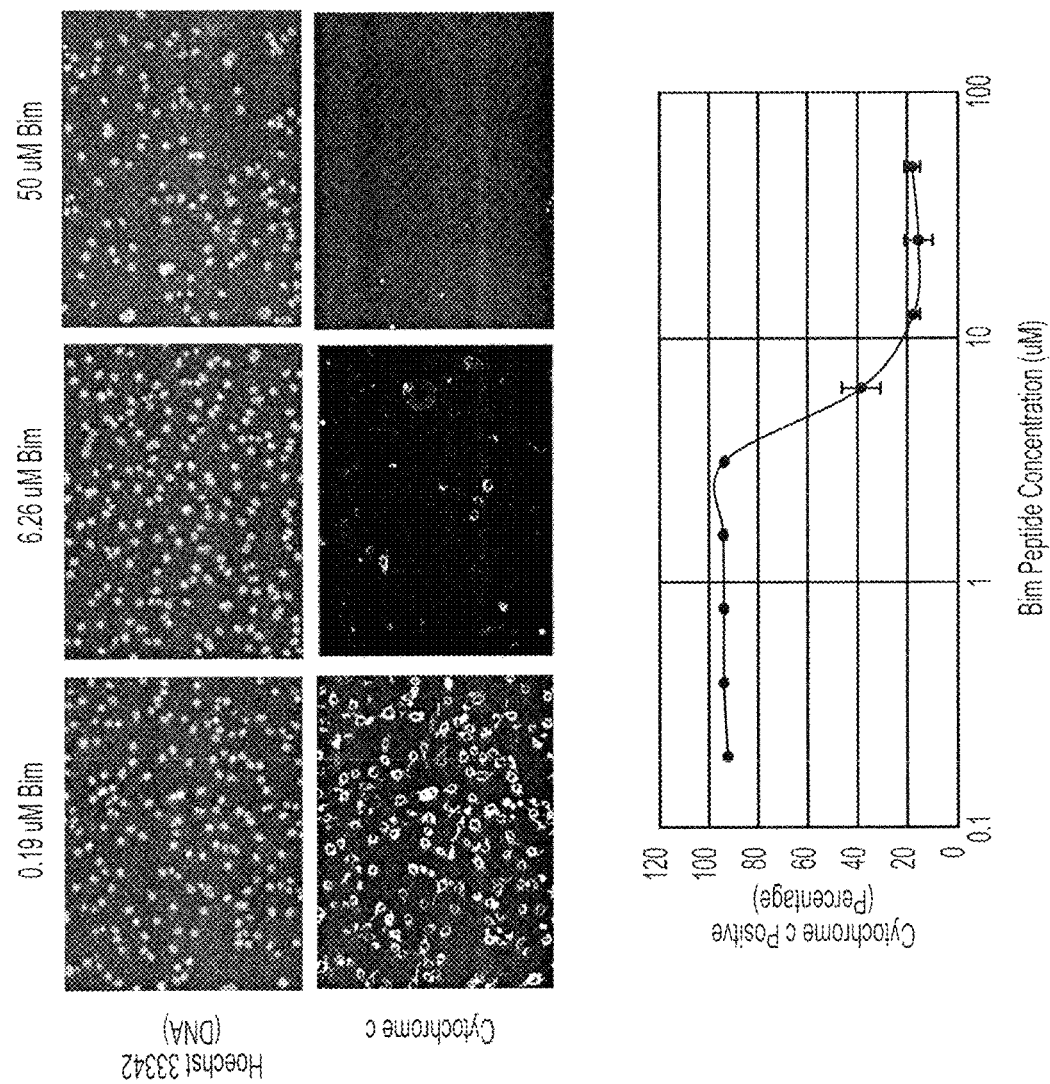
FIG. 3 depicts a dose response curve of cytochrome c loss in pancreatic cancer cell lines. The SU86.86 pancreatic cancer cell line was treated with an increasing dose of the synthetic Bim peptide. Cells were stained with a DNA dye (Hoechst 33342) and an anti-cytochrome c antibody. Progressive loss of cytochrome c occurred at higher concentrations of the peptide. Quantification of cytochrome c loss from individual cells resulted in a dose response curve with error bars representing standard deviations of triplicate wells. A 2× concentrated MEB buffer was used in this experiment.

FIG. 3 shows data from a dose response experiment in pancreatic cells. Briefly, SU86.86 pancreatic cancer cells were treated with an increasing dose of the synthetic Bim peptide and subjected to the protocol described above. Results indicate progressive loss of cytochrome c occurs at higher concentrations of the peptide. Loss of cytochrome c points to the induction of mitochondrial outer membrane permeabilization (MOMP) in the cells by the Bim peptide.

Figure 4:
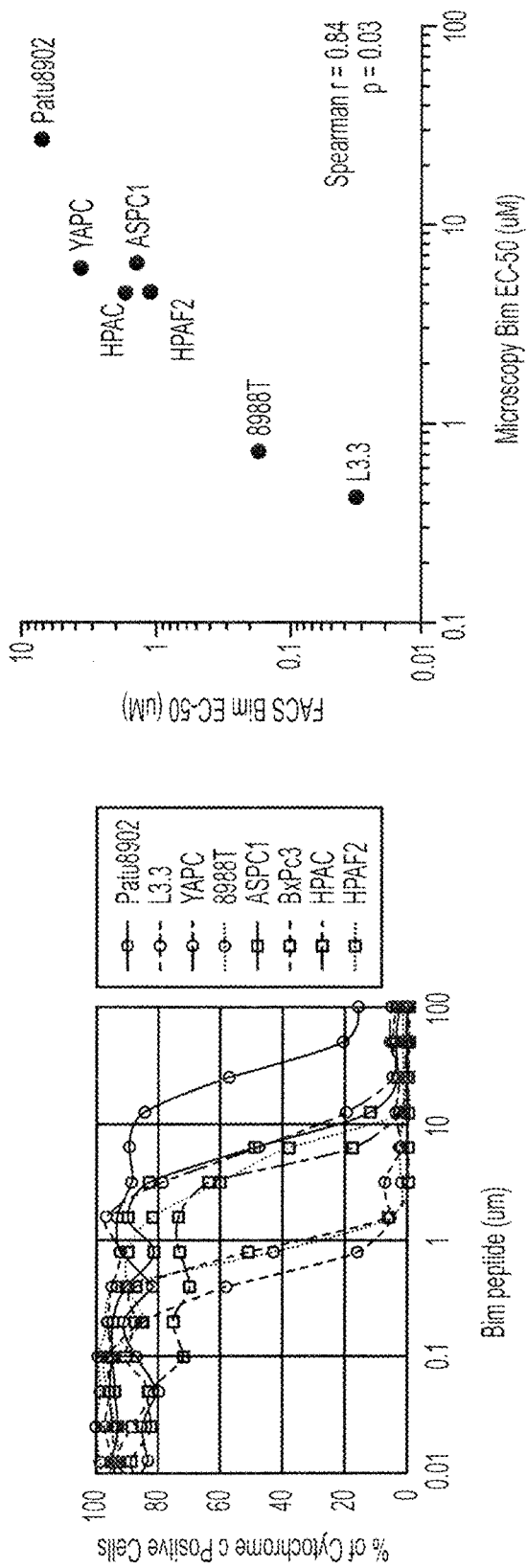
FIG. 4 shows a comparison of HTS BH3 Profile Results and FACS BH3 Profile Results for several pancreatic cancer cell lines. The EC-50's of the high throughput microscopy assay were decreased, but correlated, indicating compatibility of the assays.

High throughput BH3 Profiling provides decreased sensitivity but similar selectivity to previously used iBH3 Profiling assays. FIG. 4 shows a comparison of HTS BH3 Profile Results and FACS BH3 Profile Results. The absolute EC-50 values are systematically higher with the automated microscopy BH3 profile. This may result from a difficulty of peptide access to mitochondria. Without wishing to be bound by any particular theory, the EC-50's of the different methods of analysis are nonetheless similar, indicating backward compatibility of the assay.

Figure 5A:
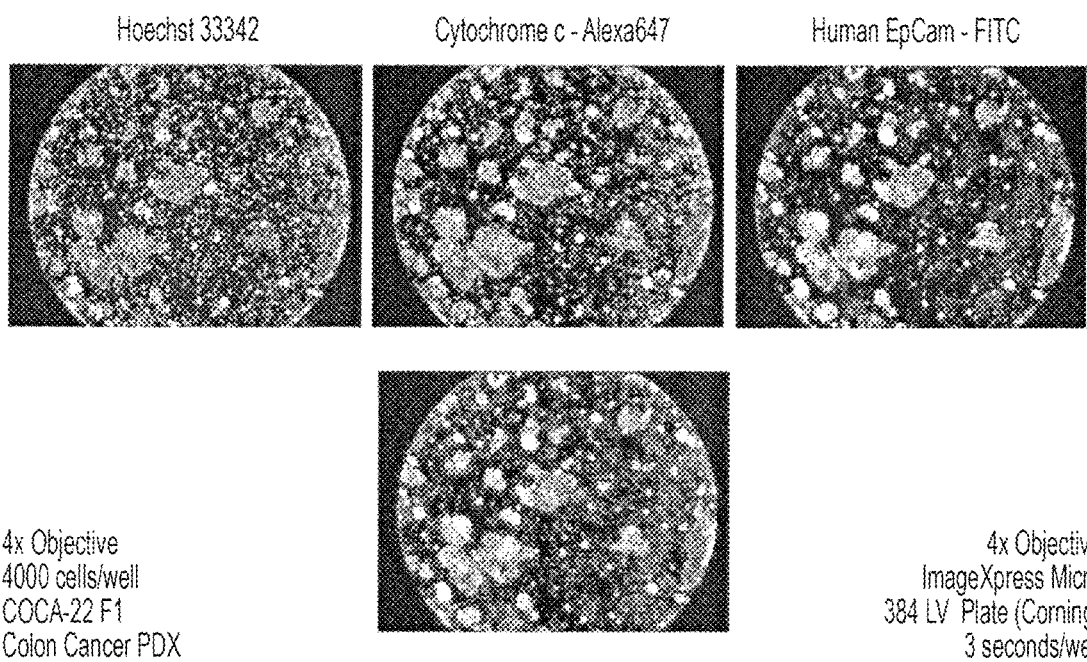
FIGS. 5A-5B show HTS BH3 Profile of cells freshly isolated from Colon PDX tumors.
Figure 5B:
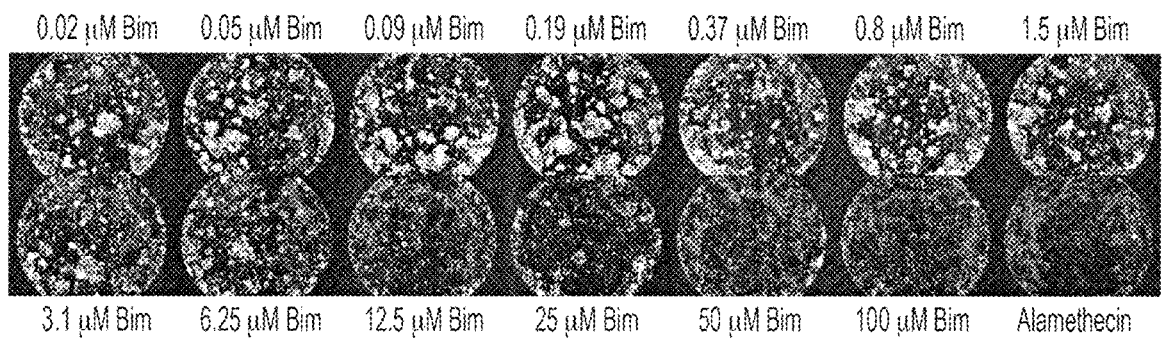
Figure 5B:
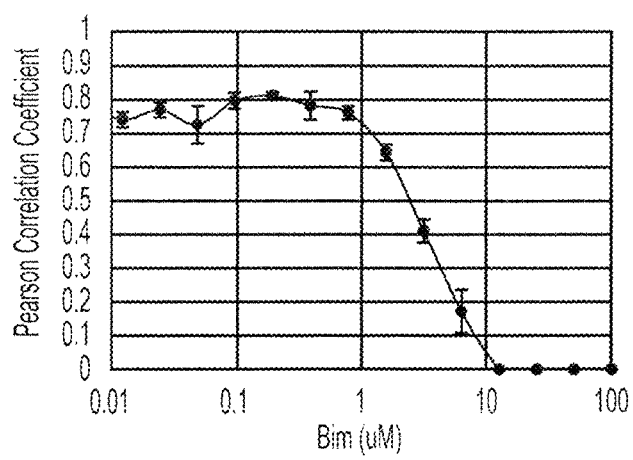
Figure 6:
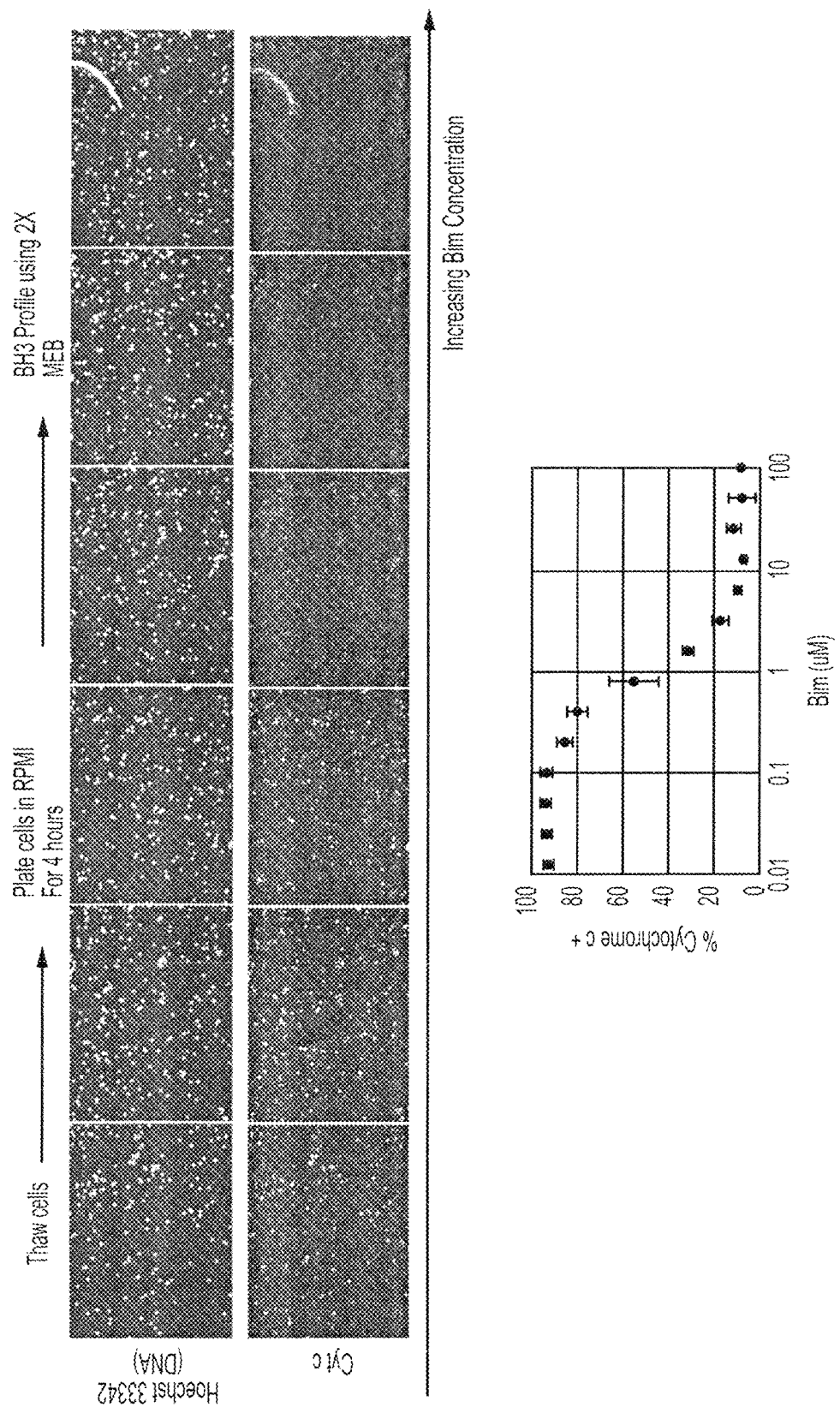
FIG. 6. shows a HTS BH3 profile of a primary human CLL tumor. Peptide-induced loss of cytochrome c is indicated by the loss of the cytochrome c signal. At bottom is a dose response curve of cytochrome c loss.
Figure 7:
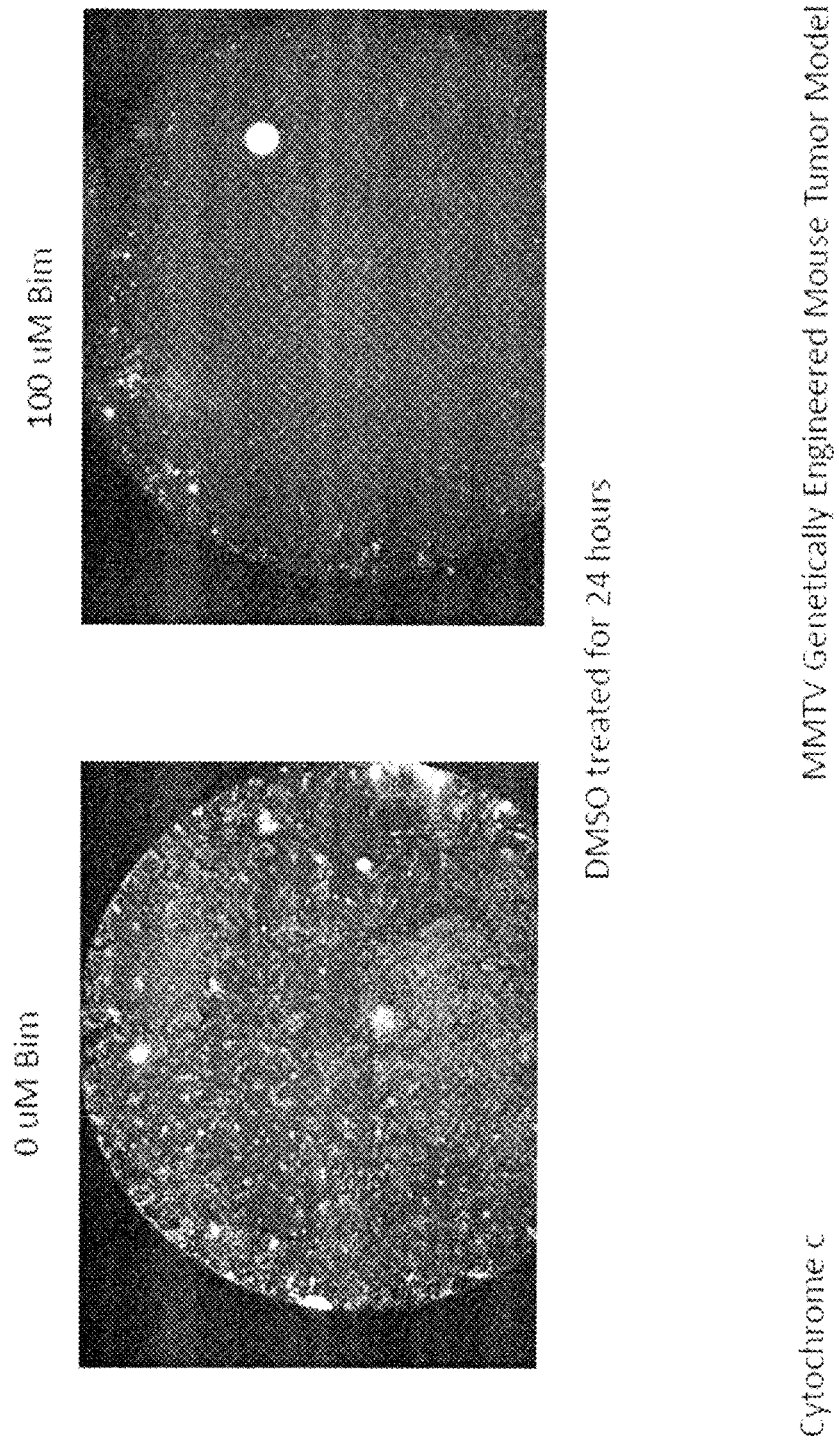
FIG. 7. shows whole well images of cytochrome c loss after a BH3 profile of cells freshly isolated from a mouse MMTV tumor that were mock treated with DMSO for 24 hours and then underwent a BH3 profile.
Figure 8A:
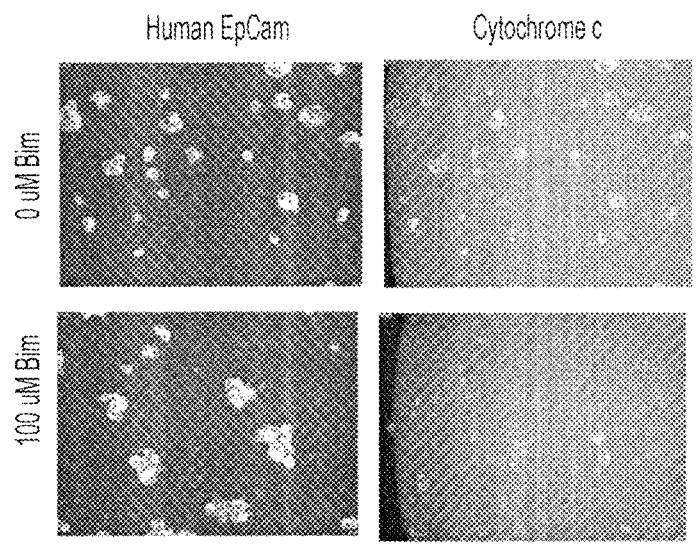
FIGS. 8A-8D show the differential staining of human tumor cells of interest from other non-tumor cells of interest.
Figure 8B:
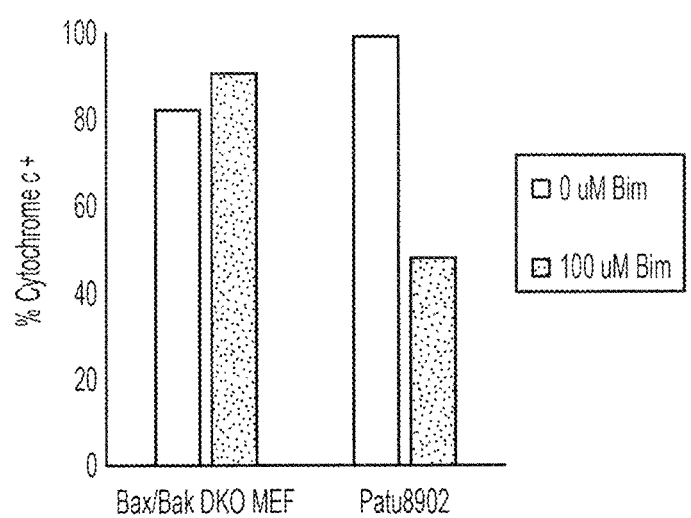
Figure 8C:
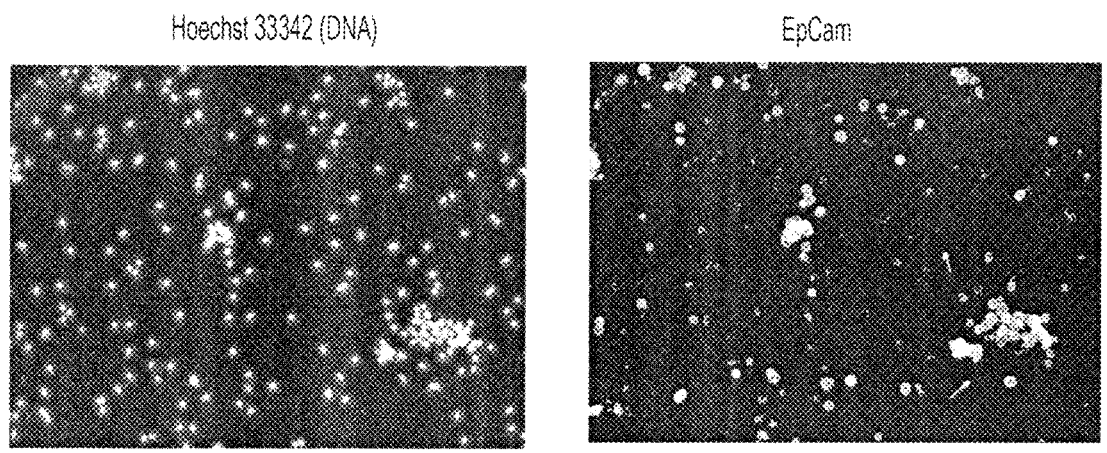
Figure 8D:
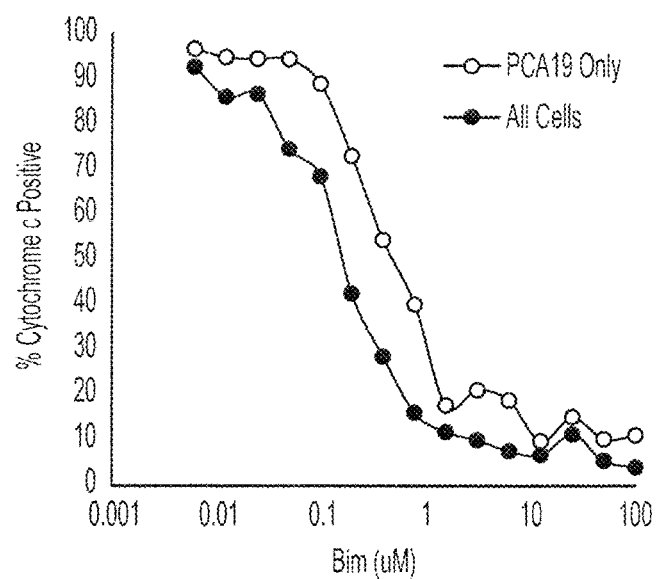

High throughput BH3 Profiling is also applicable to primary human tumor cells, cells from a PDX, and cells from genetically engineered mouse models (FIGS. 5-7). Cells of interest or tumor cells can be positively identified using tumor specific markers such as EpCam. FIG. 8 provides an example where 8902 cells are stained with EpCam and mouse Bax/Bak double knockout cells are not stained with EpCam. Additionally, FIG. 8 provides an example in which pancreatic tumor cells are differentiated from normal cells found in a pancreatic patient derived xenograft. In both examples, the difference between cells of interest and those not of interest can be distinguished, and cytochrome c release in the different populations determined.

Figure 9:
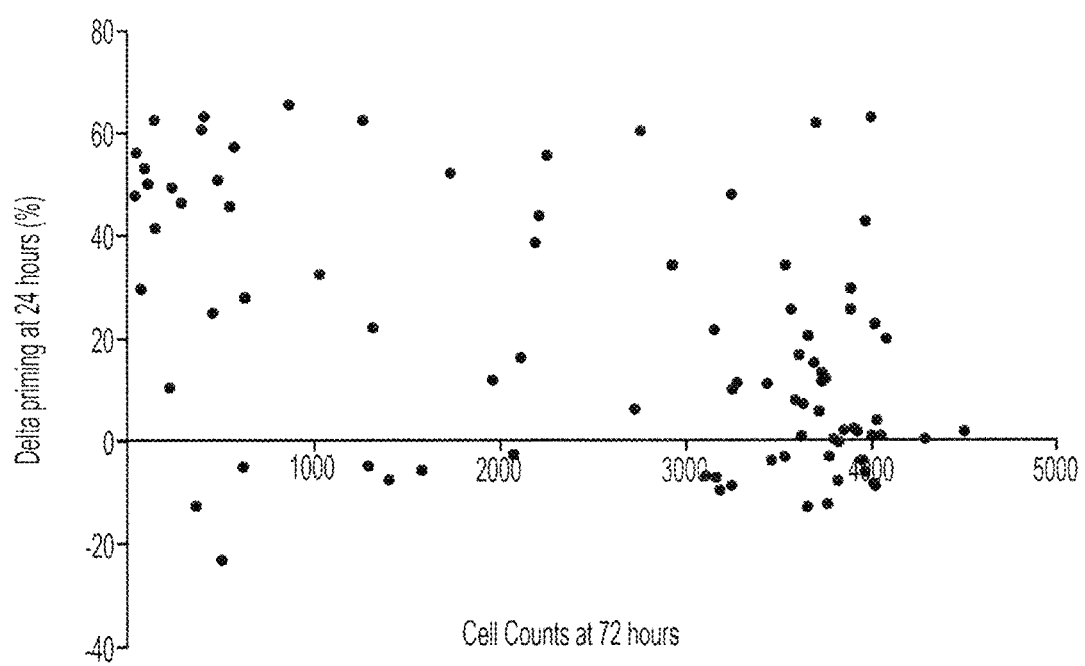
FIG. 9 shows data sets obtained by HTS Dynamic BH3 Profile. Pancreatic cancer cell line (SU86.86) were treated with different drugs for 24 and 72 hours to find drugs that increase priming at 24 hours and how this compares to cell death at 72 hours. Cells treated for 24 hours underwent BH3 profiling to identify molecules that primed cells for apoptosis. Cells treated for 72 hours were counted to reflect the number of live cells remaining. Data were generated in a single experiment.
Figure 10:
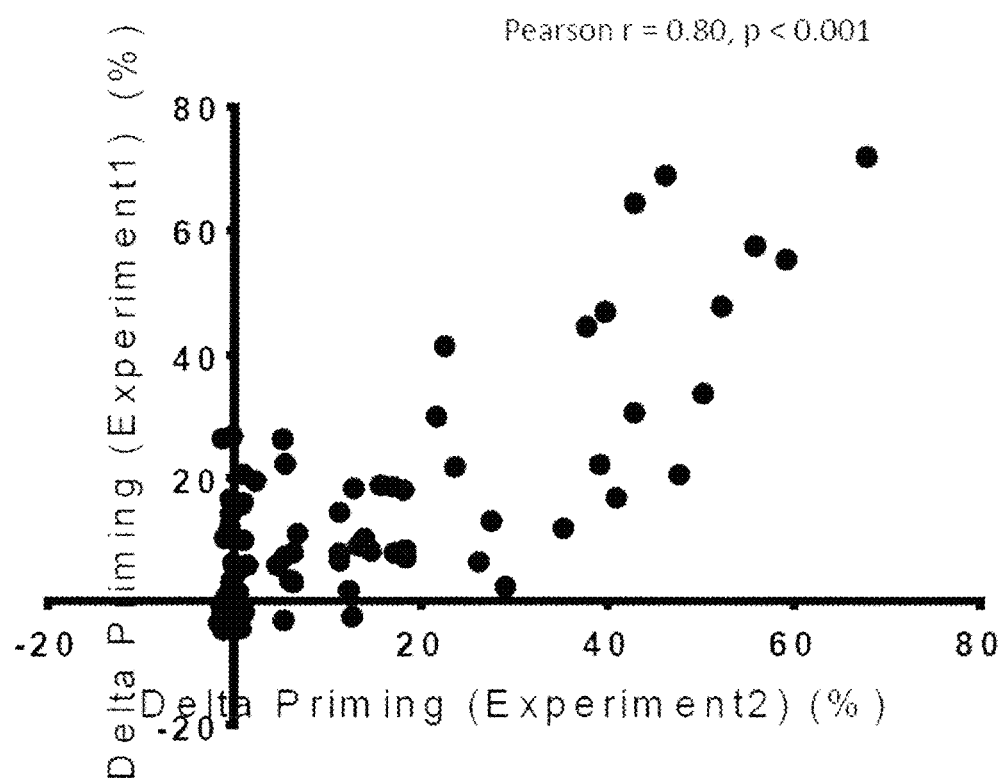
FIGS. 10A and 10B show the reproducibility of the HTS BH3 profiling assay on a cancer cell line derived from a mouse MMTV-PyMT tumor using a chemical compound library. Technical replicates are shown for the same tumor in each of FIG. 10A and FIG. 10B. Each point represents treatment with a single chemical compound.
Figure 10:
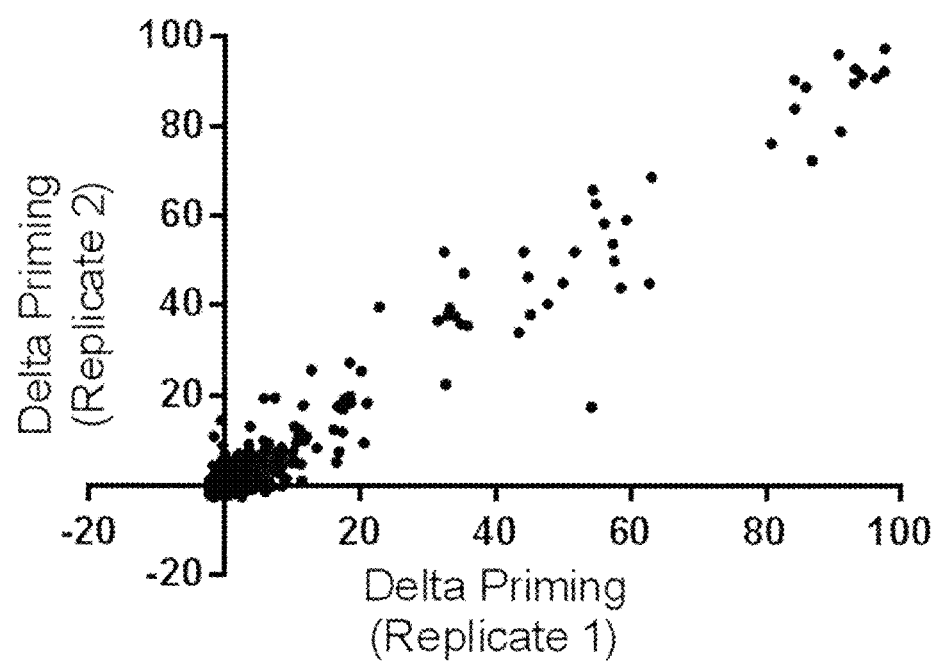

This protocol can also be used in a drug discovery context to screen a large number of compounds against either human primary tumor cells, PDX, genetically engineered mouse models or established cancer cell lines (FIG. 9). Notably, data shown in FIG. 9 was compiled in a single experiment, whereas earlier versions of the BH3 Profile required weeks to acquire comparable amounts of data. Moreover this data is reproducibly produced from different biological experiments on the same cell line (FIGS. 10A-10B).

The High Throughput BH3 Profiling protocol overcomes many challenges faced by currently used BH3 Profiling methods. First, the need to remove cells from culture plates for wash and staining steps has been eliminated. The new method keeps the cells in culture wells and also adherent for optimal imaging during the addition of BH3 Profiling buffers (DTEB or MEB, formaldehyde, neutralizing buffers, staining solutions). This was achieved by using two advances. First extracellular matrix coated plates, or antibody coated plates kept the cells attached during BH3 profiles. Extracellular matrix coated plates have the additional benefit of producing better cell viability during the drug incubation. Furthermore, the use of adhesive surfaces facilitates high quality microscopy by keeping cells in the imaging plane, and facilitates post antibody staining washes to reduce fluorescence background.

Figure 2:
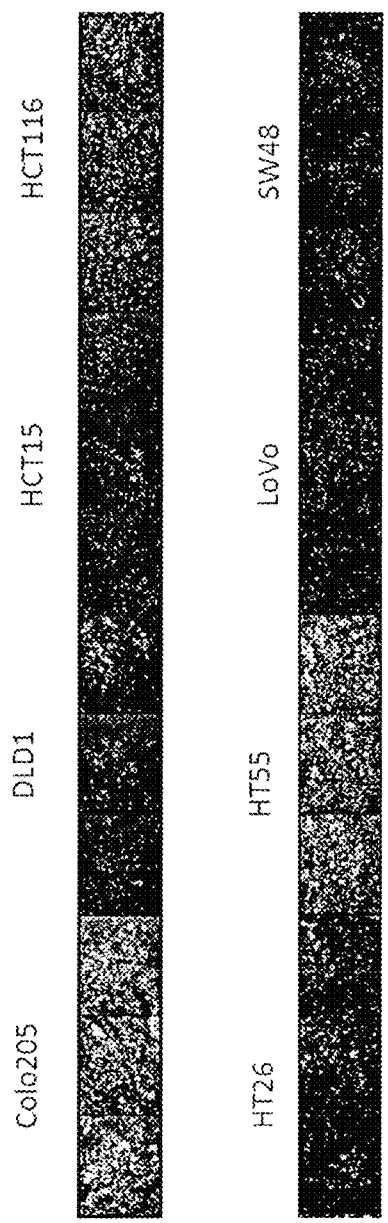
FIG. 2 depicts the effect of aspirating and washing media from live cells in 384 well plates with a low residual volume (less than 5 μL). Several colon cancer cells were plated on tissue culture treated plates and underwent high-throughput screen (HTS) BH3 profiling one day later. Note that some cells are retained after the wash, and other cells are lost. This is a well-known problem of using plate washers with low residual volume. Cells are stained with a cytochrome c antibody.

Second, instead of performing wash steps where little or no media is left behind and which can result in significant cell loss (FIG. 2), the discovery that BH3 profiling can be performed with concentrated buffer allows the wash step in the assay to be performed with high amounts of residual volume left in the well. The relatively high amount of residual volume facilitated by the use of concentrated buffer resulted in increased numbers of residual cells, possibly by reducing the shear force or pressure applied to the cell otherwise experienced with low residual volumes.

Another significant difficulty overcome by the High Throughput BH3 Profiling protocol is the addition of peptides into wells with the BH3 profiling buffer. This is a time sensitive step because mitochondrial outer membrane permeabilization occurs within one hour after the peptides are added. Yet, in a drug screening context, between 2-4 peptide concentrations of each drug are tested, meaning that different peptide concentrations need to go into each well. The use of multichannel pipettes does not provide a scalable approach. The high throughput method described here solves that problem by utilizing 384 well pinning machines and digital drug printers (HP D300) to add peptides to the culture plate in a rapid manner.

Figure 11:
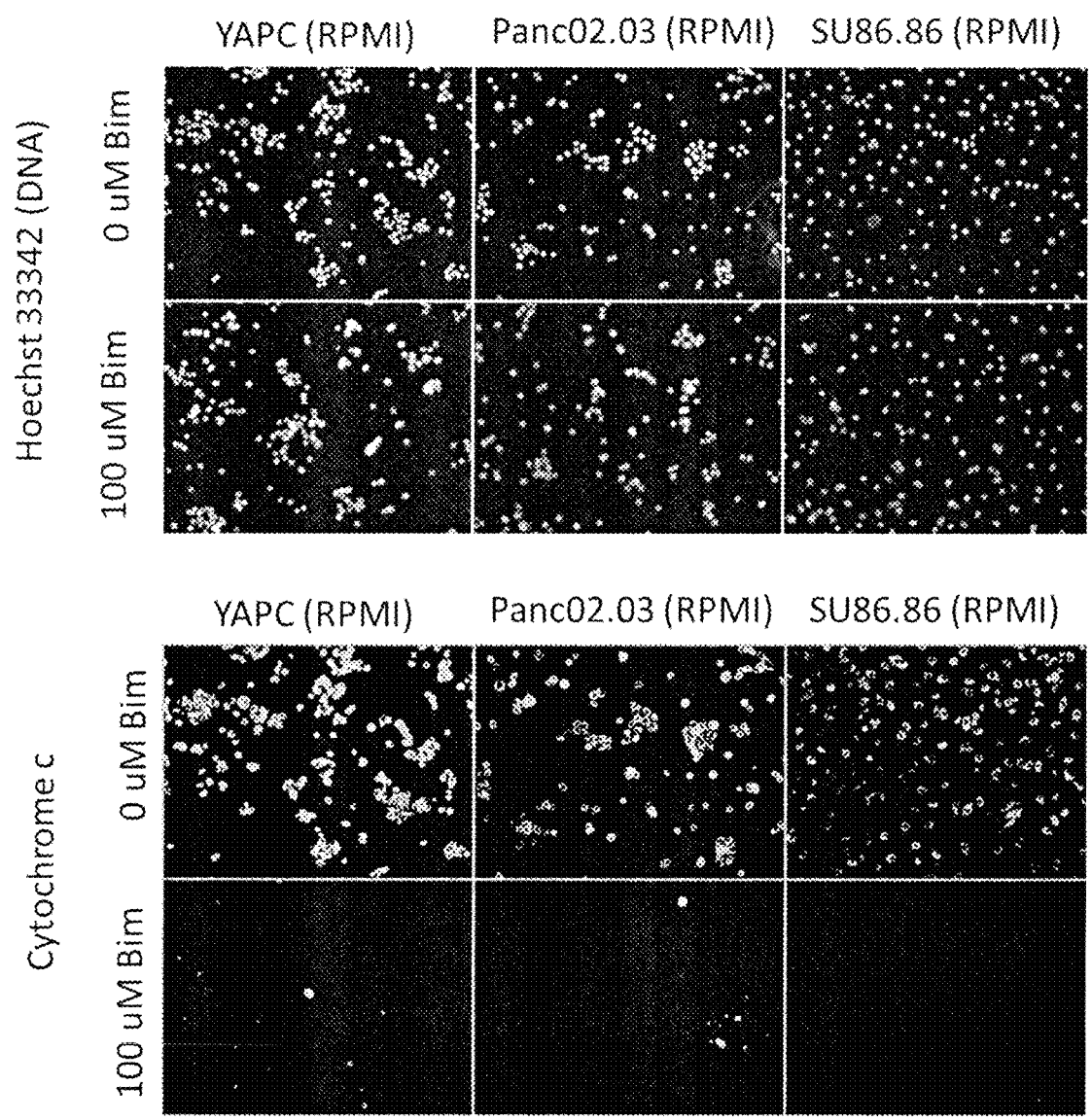
FIGS. 11A-11C show examples of response to Bim peptide with 2× buffer concentrate across several pancreatic cancer cell lines. Cells were stained with anti-cytochrome c antibody and Hoechst 33342 dyes.
Figure 11:
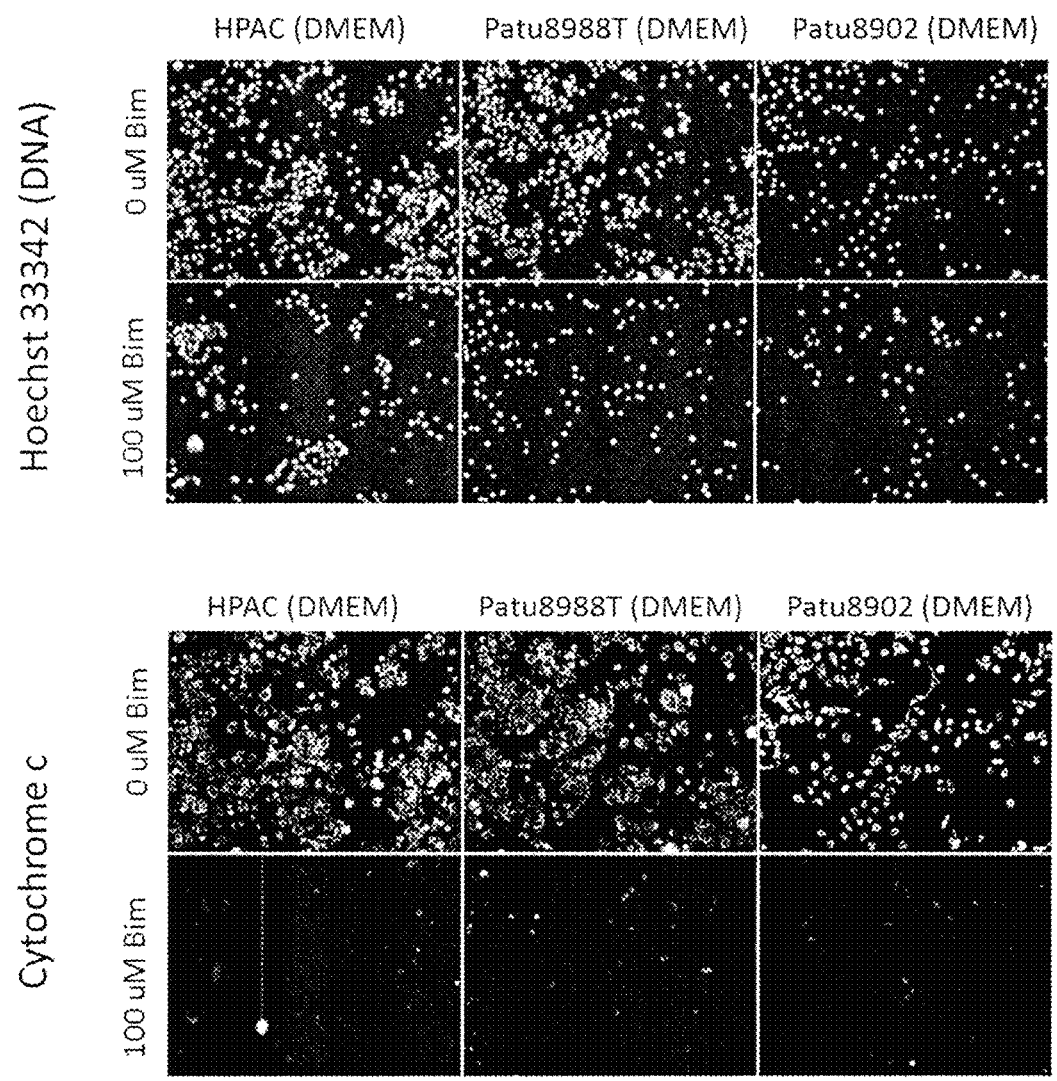
Figure 11:
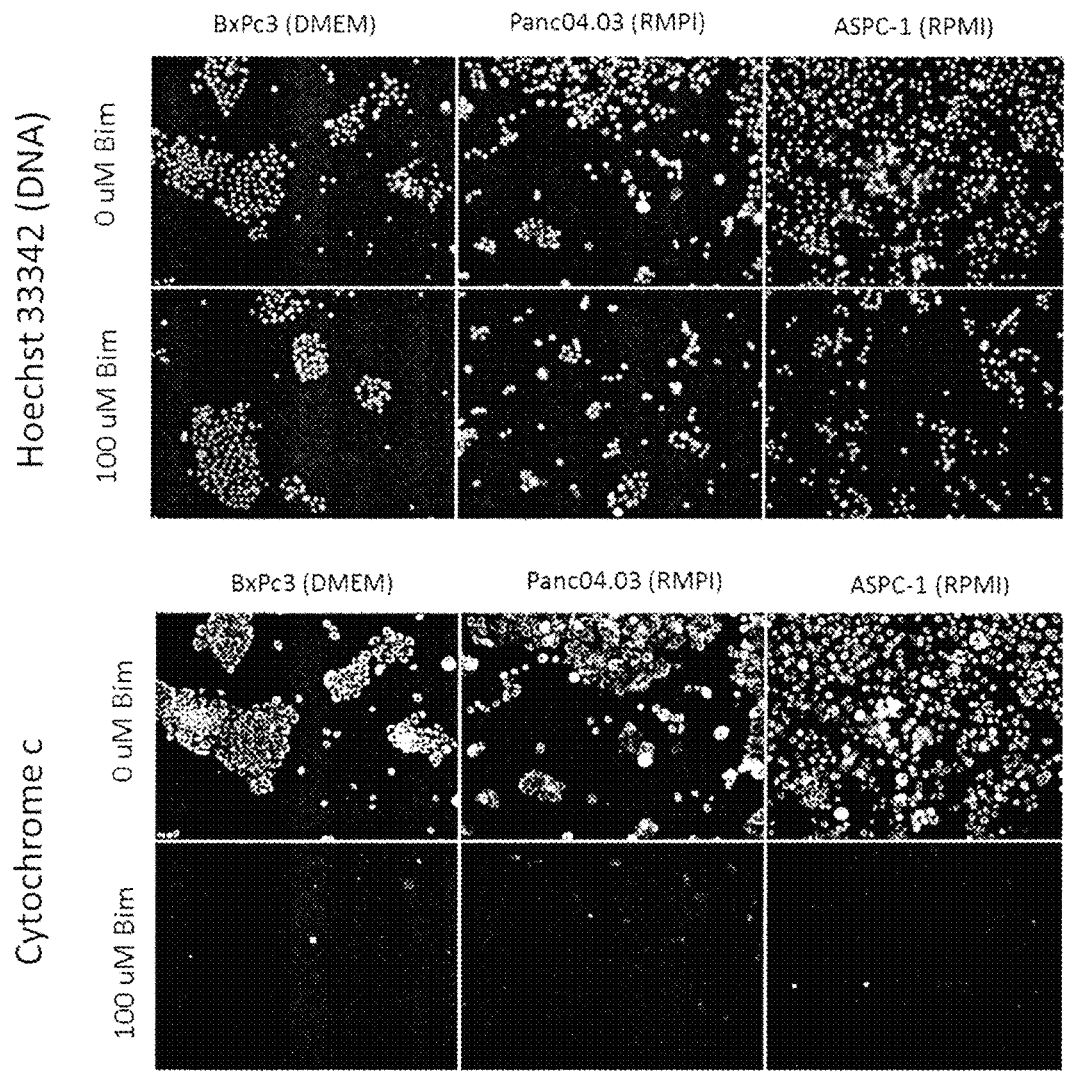

The High Throughput BH3 Protocol also tolerates the use of several buffer concentrations across a variety of cancer cell lines. All experiments were performed in the presence of culture media containing serum or PBS. FIG. 3 shows dose response curve data for a pancreatic cancer cell line (SU86.86) generated using several concentrations of Bim peptide in a 2× concentrated buffer. FIGS. 11A-11C show the response of several cancer cell lines to 100 μM Bim peptide in 2× buffer. Treatment of all cell lines with Bim in 2× buffer resulted in cytochrome c loss as measured by fluorescence microscopy.

Figure 12:
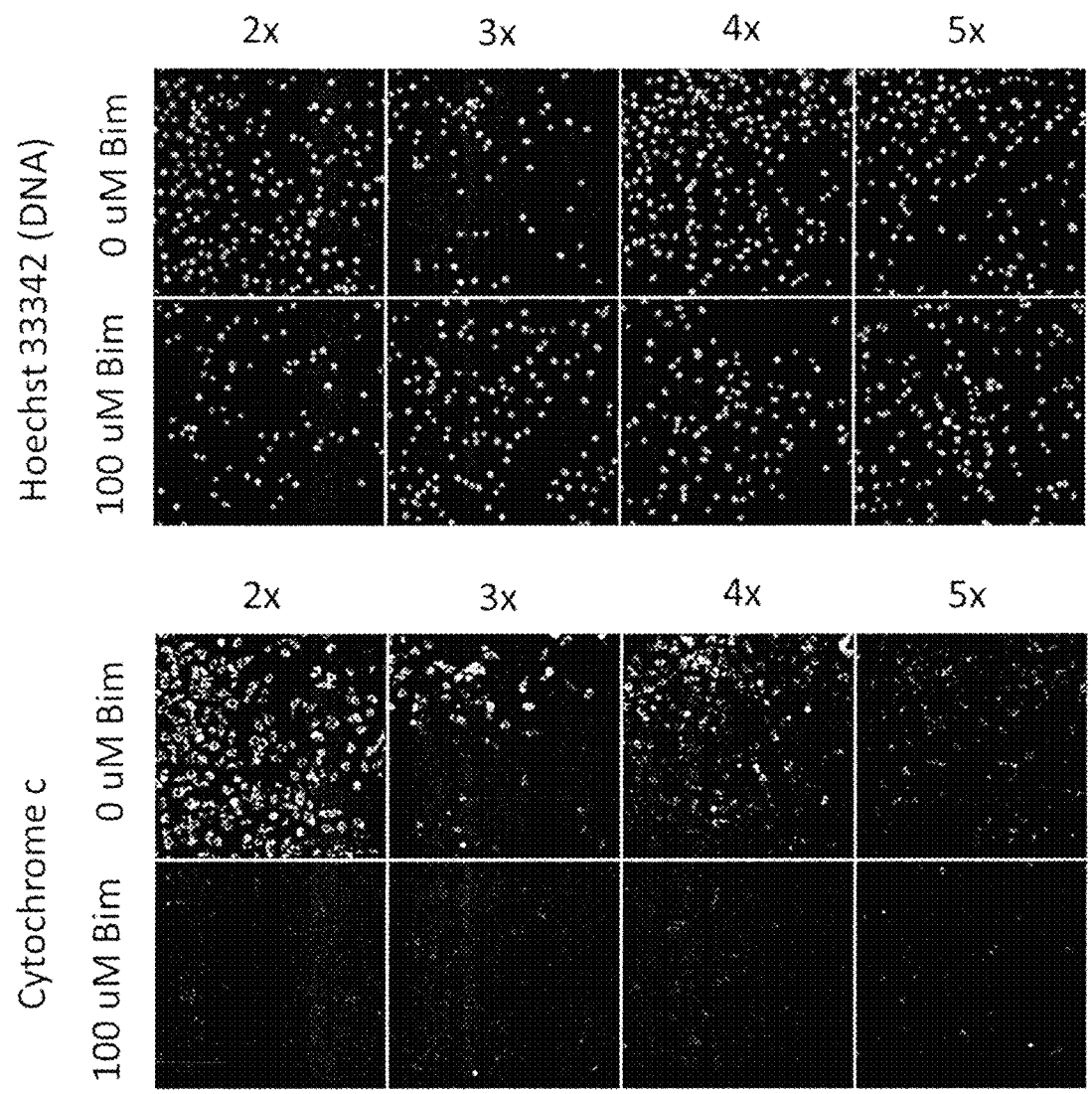
FIGS. 12A-12B show treatment of pancreatic cancer cell lines with either 0 μM Bim peptide or 100 μM Bim peptide in several buffer concentrations.
Figure 12:
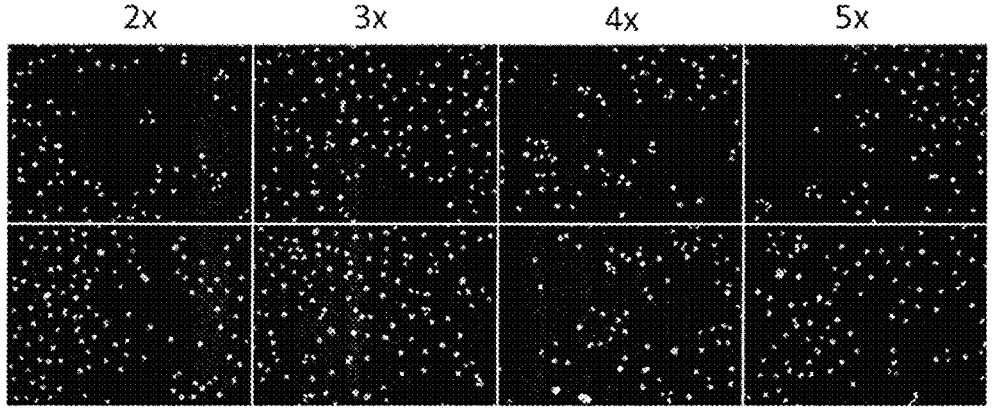
Figure 12:
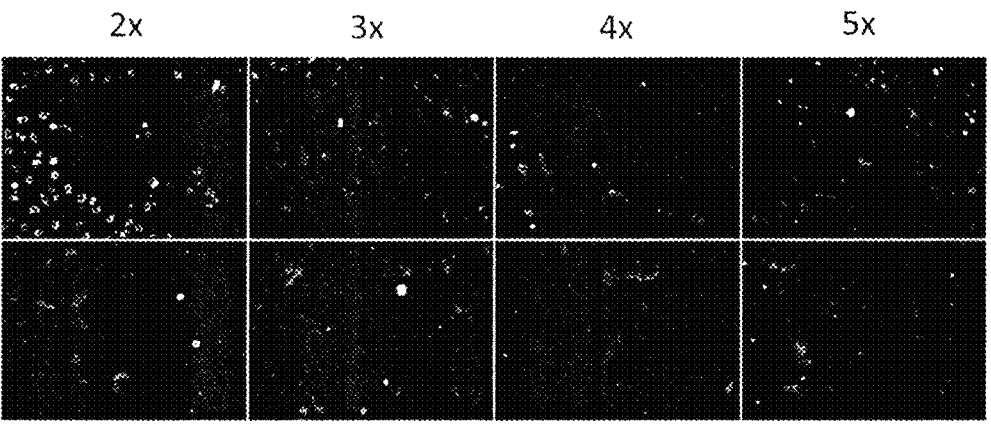

FIG. 12 shows adherent pancreatic cancer cell lines treated with 100 μM Bim peptide in 2×, 3×, 4× and 5× buffer and then measured by fluorescence microscopy. Non-specific cytochrome c loss occurs at concentrations about 3× and higher, whereas peptide induced cytochrome c loss only occurred with the 2× buffer.

Figure 13A:
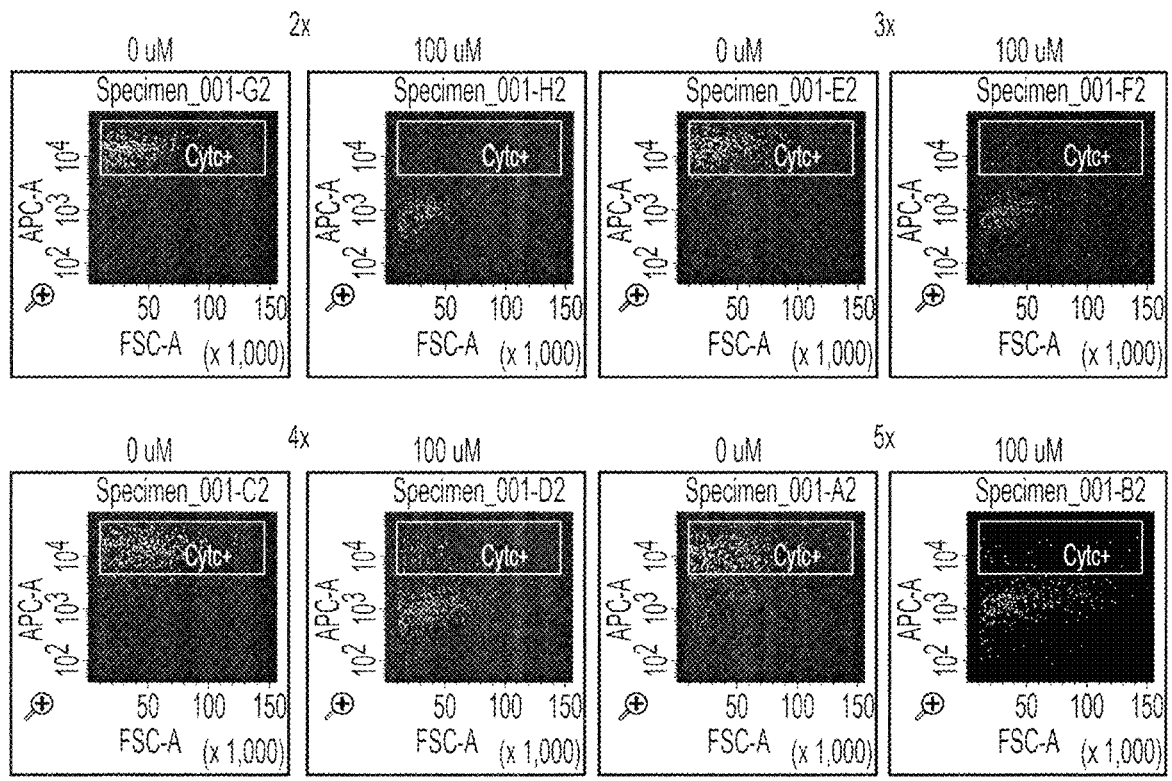
FIGS. 13A-13B show treatment of pancreatic cancer cell lines with either 0 μM Bim peptide or 100 μM Bim peptide in several buffer concentrations.
Figure 13B:
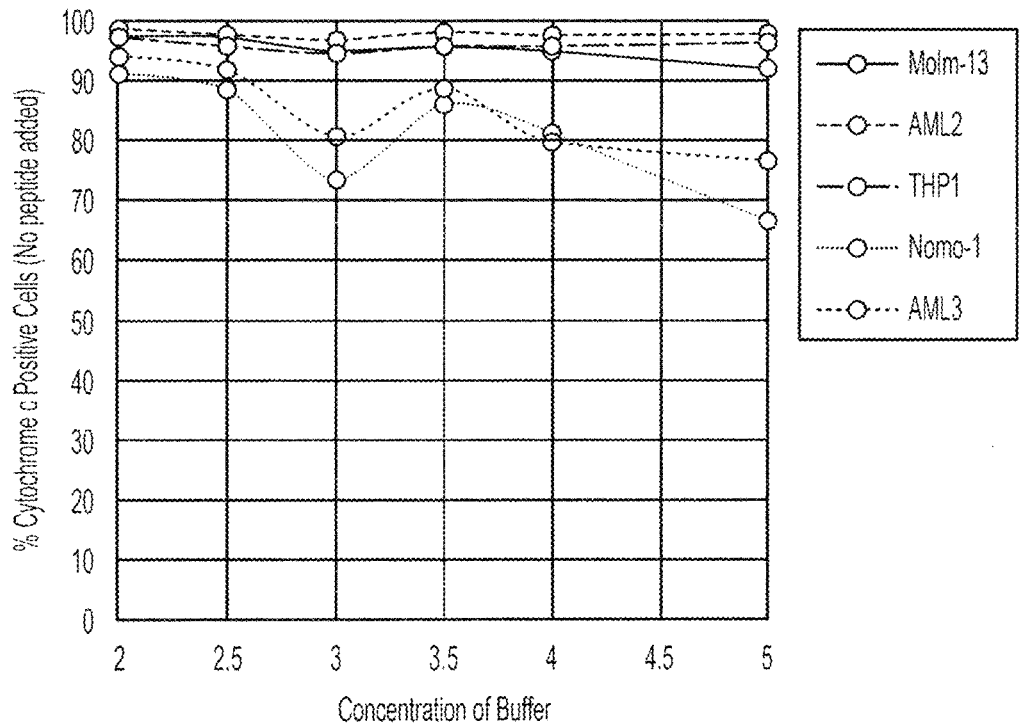

FIG. 13 demonstrates that buffer concentrations between 2× and 3× have acceptable toxicity profiles for all tested suspension cell lines and buffer concentrations up to 5× are not toxic to some cell lines (e.g., MOLM-13, AML2, THP1).

Figure 14:
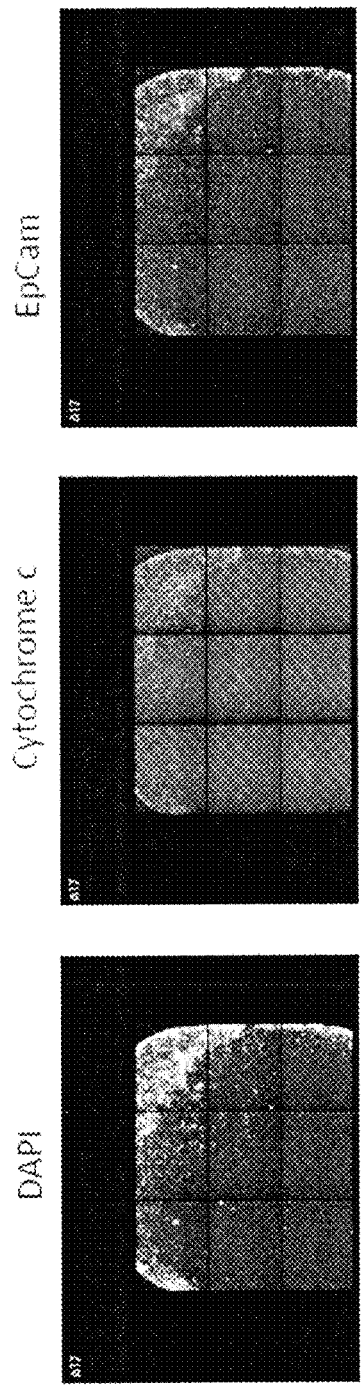
FIG. 14 shows the effect of poor cell attachment on high throughput microscopy BH3 images. Cells isolated from a colon cancer PDX was placed on a tissue culture treated cell surface and did not adhere. Due to the washes in the well, the cells were displaced to the side of the well.
Figure 15:
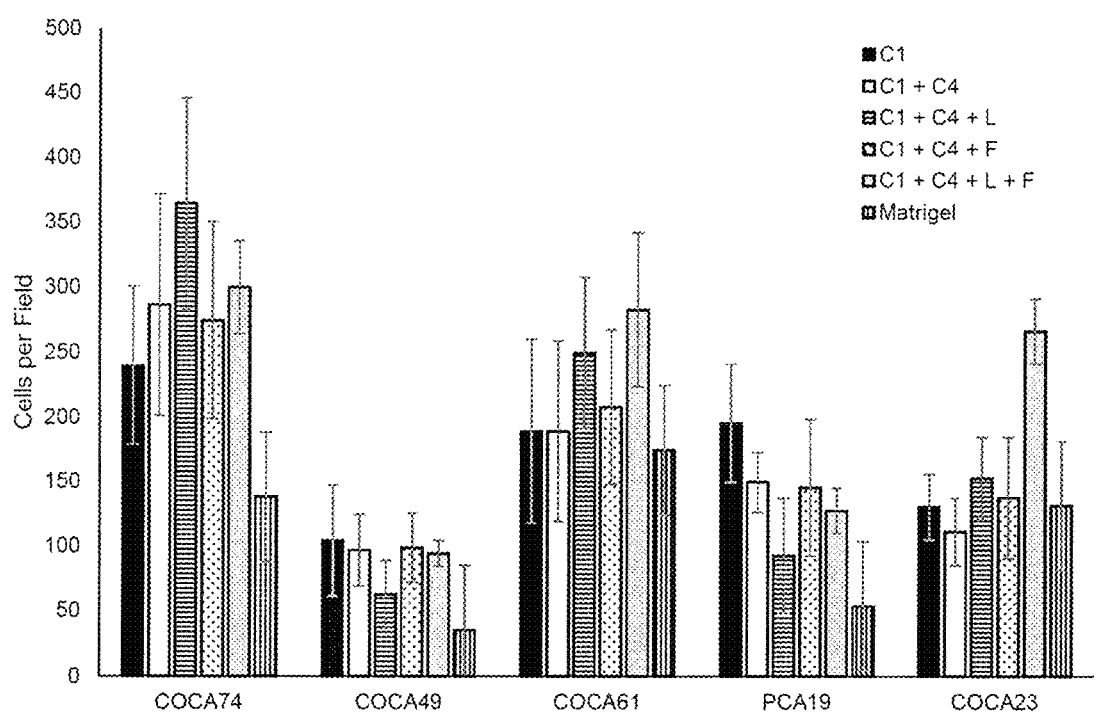
FIG. 15 shows that tumor cells from colon cancer and pancreatic cancer patient derived xenografts stuck to different extracellular matrix coated surfaces. C1 is collagen 1; C4 is collagen 4; L is laminin; F is fibronectin; Matrigel is a mixture of ECM proteins of unknown composition.
Figure 16:
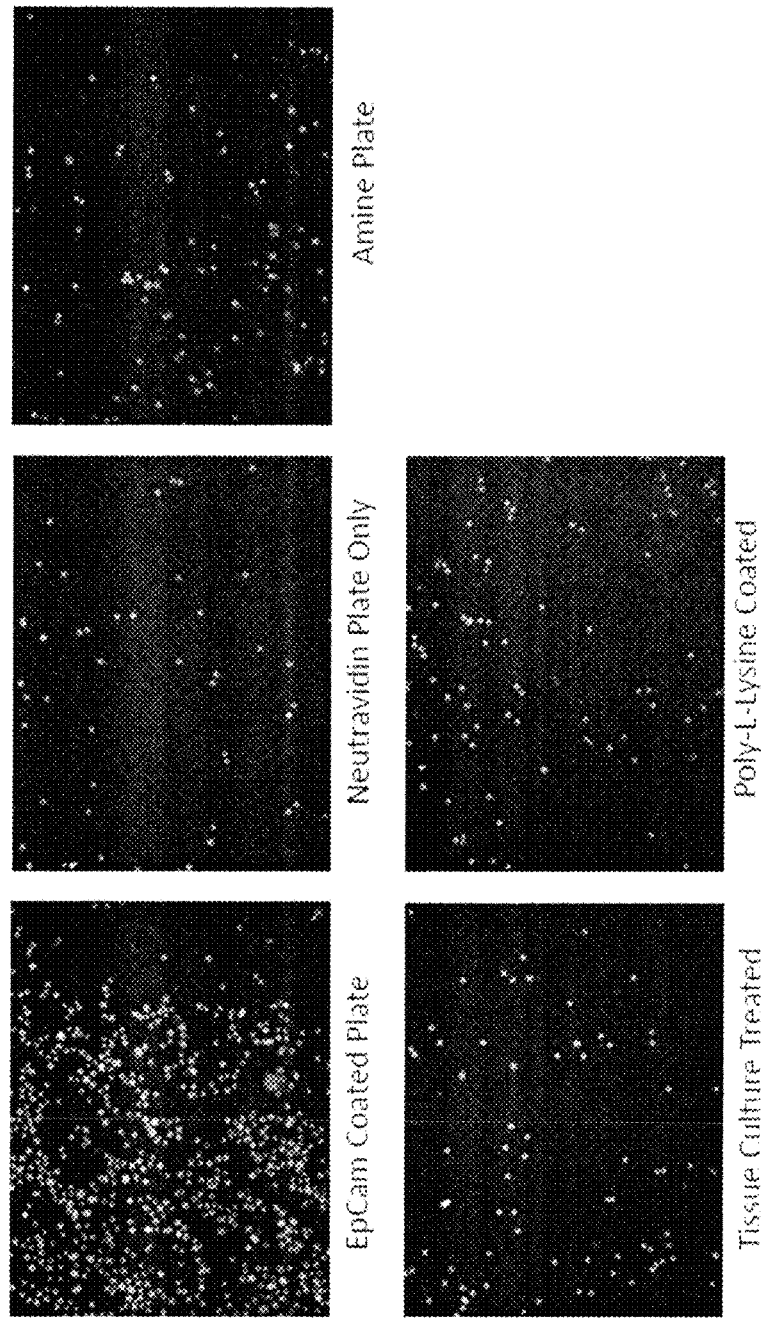
FIG. 16 shows that primary ovarian ascites stuck to EpCam coated plates during BH3 profiles, and not to neutravidin coated plates, amine plates, tissue culture treated plates, or poly-1-lysine plates. Cells are stained with the DNA dye Hoechst 33342.
Figure 17:
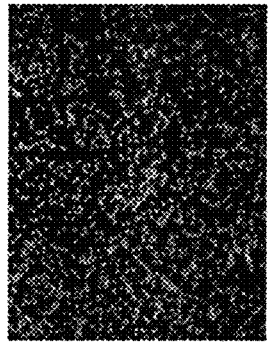
FIG. 17 shows that primary CLL tumors stuck to CD19 coated plates, amine plates, tissue culture treated plates, or poly-1-lysine plates. Cells are stained with the DNA dye Hoechst 33342.
Figure 17:
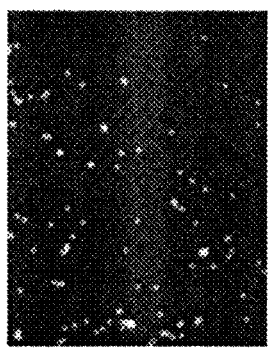
Figure 17:
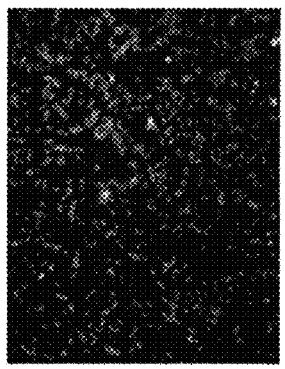
Figure 17:
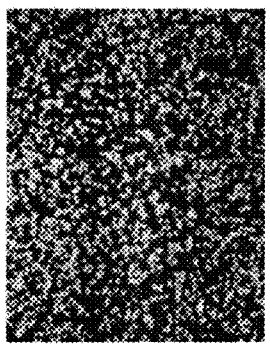
Figure 17:
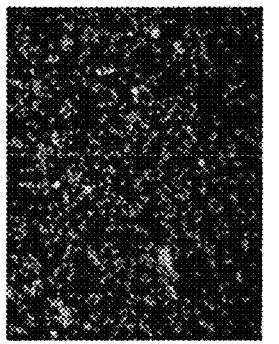

Although the BH3 profiles can be run on cells in suspension in this format, the absence of cell attachment prevents adequate data quantification using the microscopy based analysis. For example FIG. 14 is an example of colon cancer PDX cells that were not attached prior to drug treatment or BH3 profiling. The cells aggregate in the corner of the wells. Although this is not a terminal problem for FACS analysis, these clusters of cells are not amenable to microscopy based analysis. In contrast, the colon cancer PDX images in FIG. 5 are plated on collagen I coated plates, and are distributed equally throughout the well, and are amenable to microscopy based analysis. In addition to collagen I coated surfaces, several extracellular matrix coated surfaces facilitate the adhesion of tumor cells (FIG. 15). For known suspension tumors, antibody coated plates facilitate attachment to the cell surfaces after a BH3 profile and therefore better quantification. An example of enhanced attachment is provided using ovarian ascites tumors and CLL tumors (FIG. 16 and FIG. 17, respectively).

Figure 18:
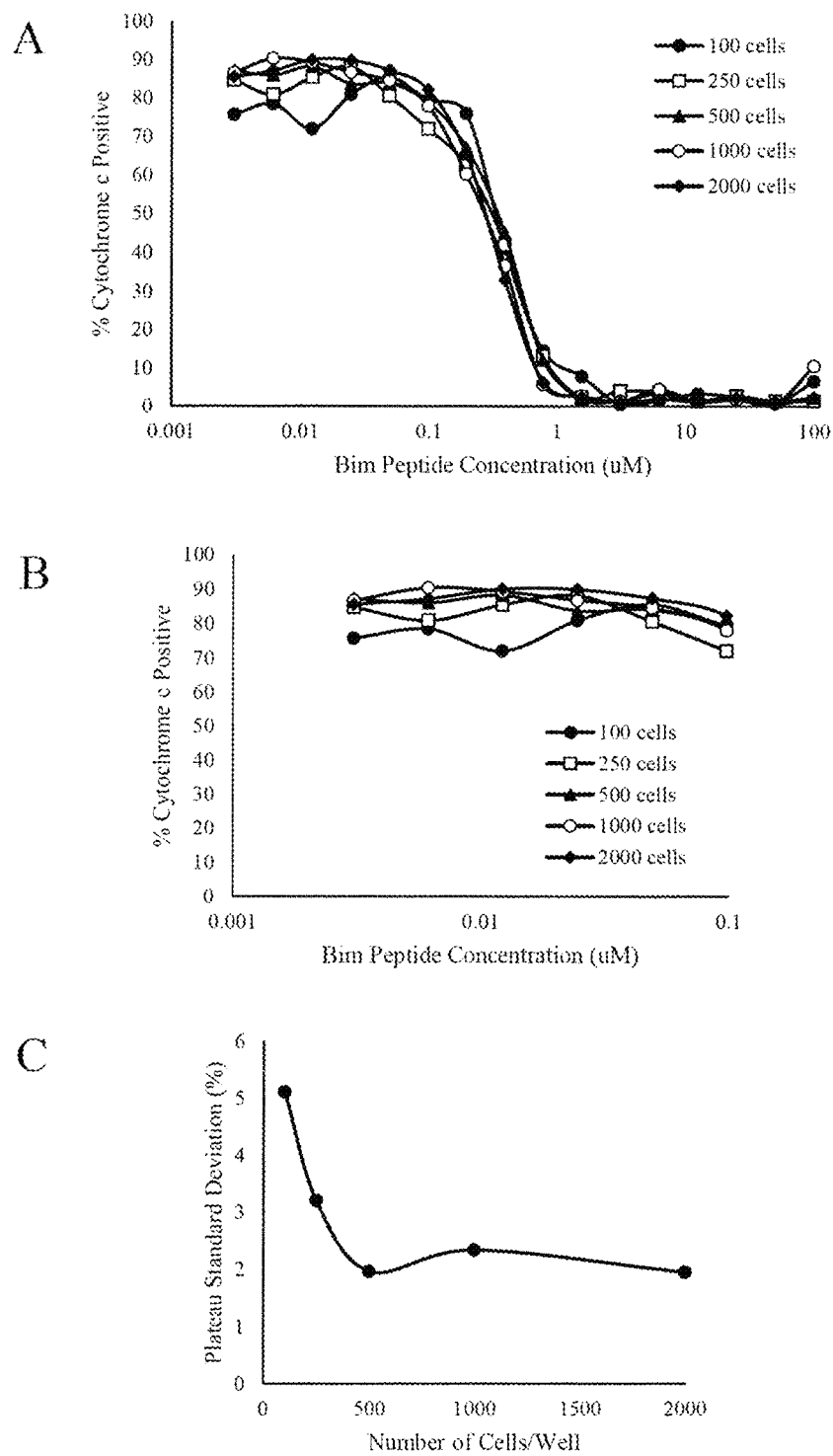
FIGS. 18A-18C show that HT-DBP can be performed with as few as 100 cells with differing degrees of noise. Here, a pancreatic cell line was plated at different cell numbers per well and subjected to a high throughput BH3 profile.
Figure 19:
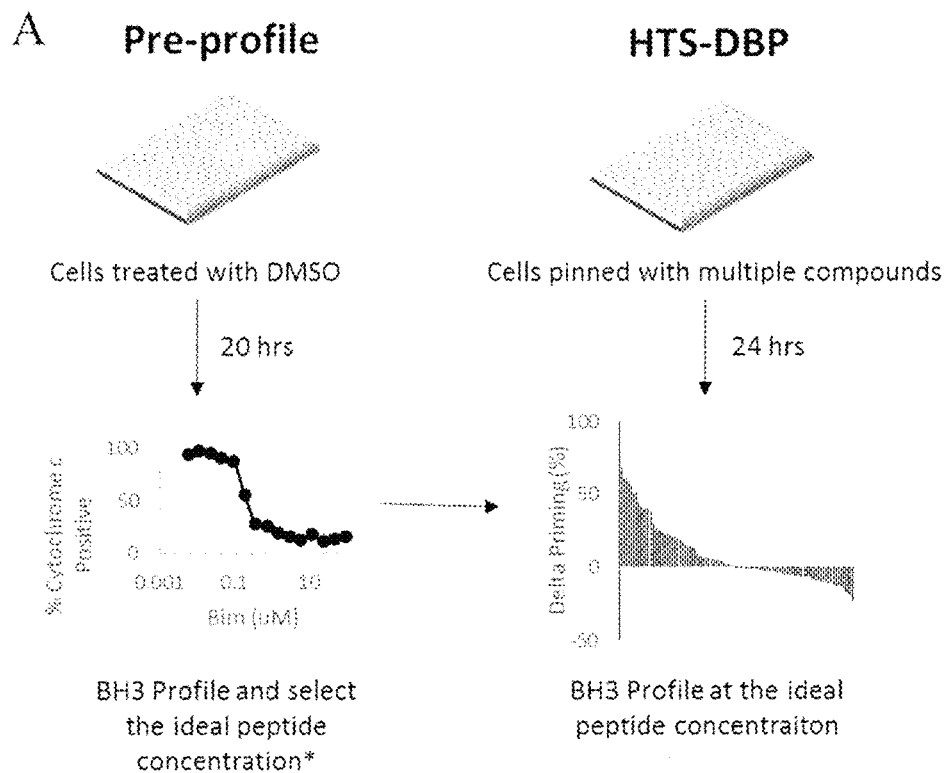
FIGS. 19A and 19B show that pre-BH3 profiles identified the single and correct peptide concentration used for HT-DBP using tumor cells isolated from an MMTV-PyMT mouse mammary tumor. For many tumors, the apoptotic priming will not be pre-determined. This includes tumors that cannot be frozen. In these instances, it is important to identify the ideal peptide concentration to perform HT-DBP to reduce the minimum number of cells required for HT-DBP. It was found that a HT-DBP pre-profile and a BH3 profile performed 4 hours apart yielded similar levels of apoptotic priming.
Figure 19:
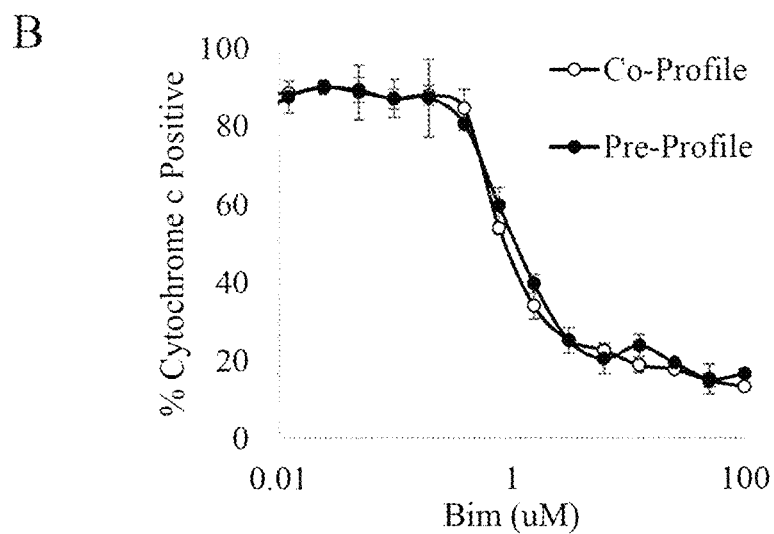

As compared to earlier iterations of dynamic BH3 profiling, HT-DBP works effectively with few numbers of cells. An example of an HT-DBP with as few as 100 cells is provided in FIG. 18. A further reduction in the number of cells required is performed using a pre-BH3 profile outlined in FIG. 19 to identify the single BH3 peptide concentration to perform the chemical compound screen. This pre-profile is often performed 4 hours prior to the BH3 profile used for the chemical compound screen. Note that in FIG. 19B that the pre-BH3 profile overlaps perfectly with a BH3 profile 4 hours later.

Figure 20:
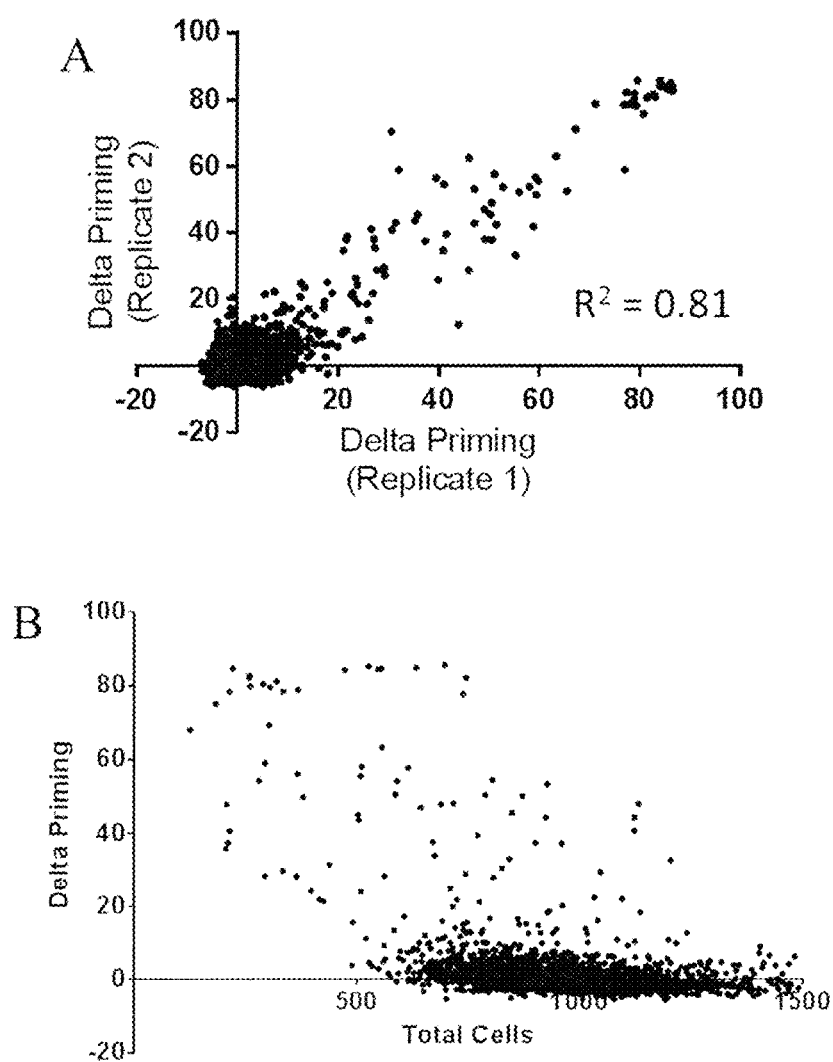
FIGS. 20A-20C show a HT-DBP of MMTV-PyMT mouse tumors using a chemical compound library.
Figure 20:
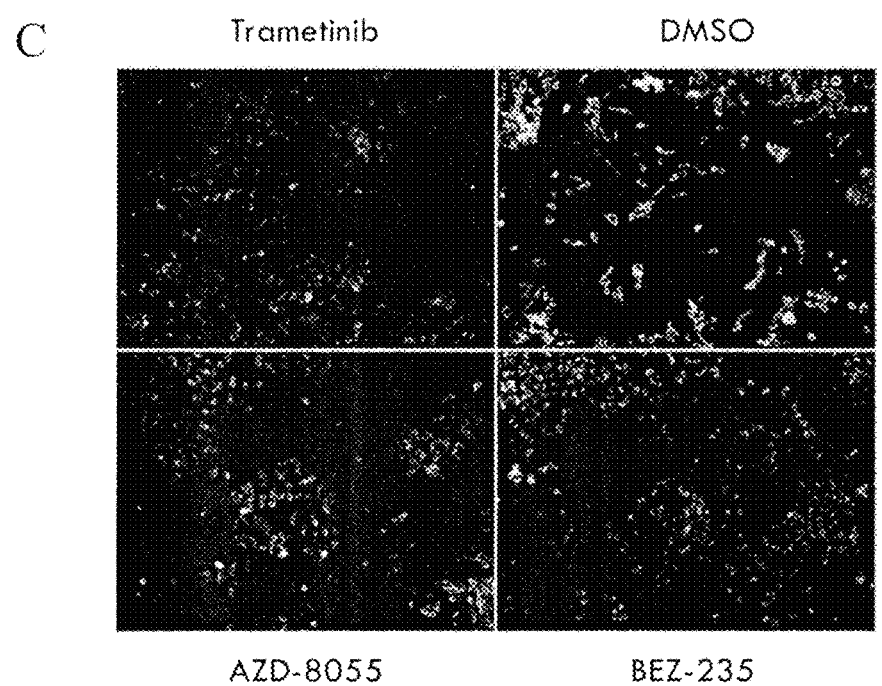
Figure 21:
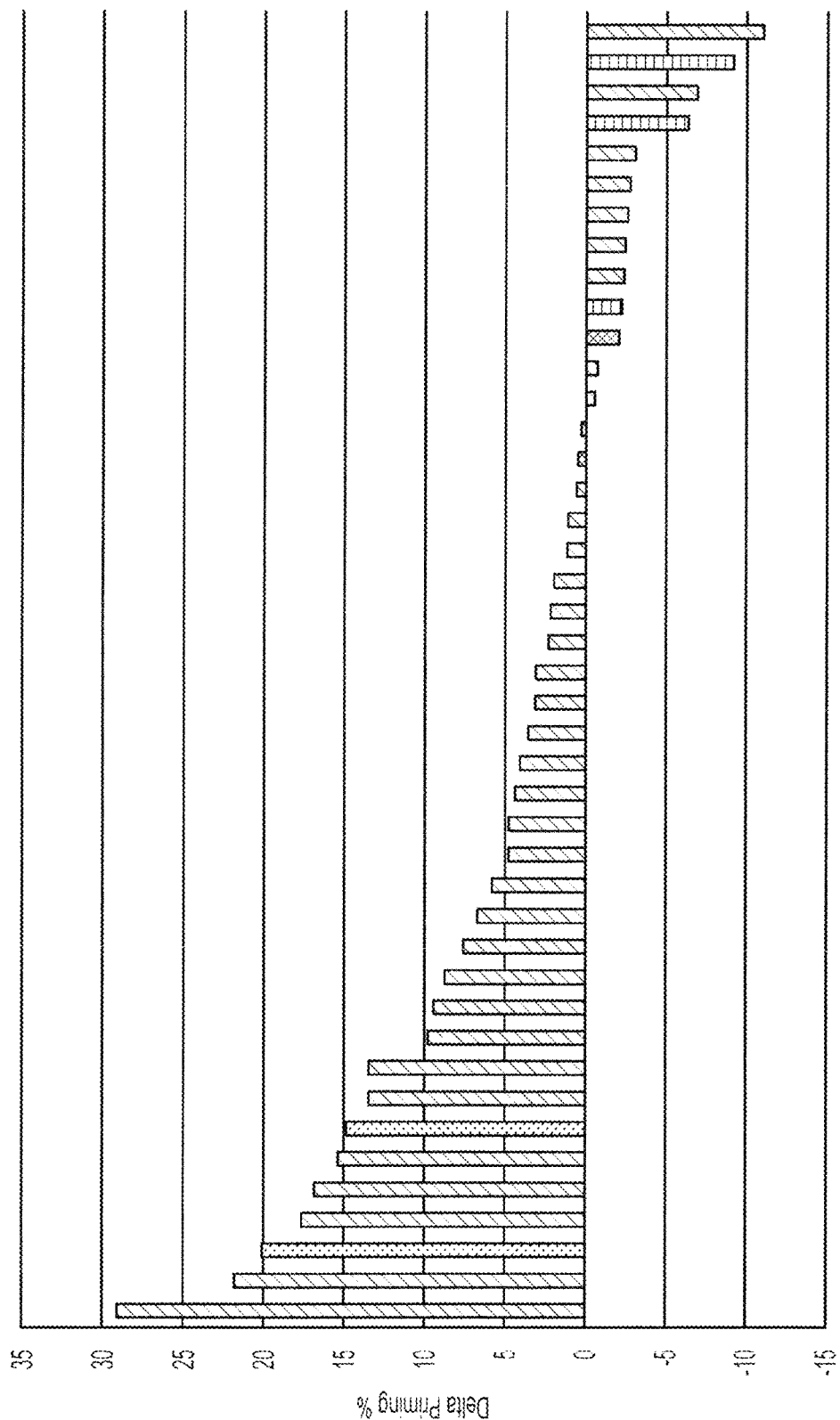
FIG. 21 shows examples of a high throughput dynamic BH3 profile on a select number of drugs on a primary ovarian ascites tumors. The drugs that caused the greater delta priming are those that are likely to increase chemosensitivity. Bars 3 and 7 depict (from left) drugs that have a similar mechanism of action. Bars 34, 40, and 42 (from left) depict drugs that have a similar mechanism of action.
Figure 22:
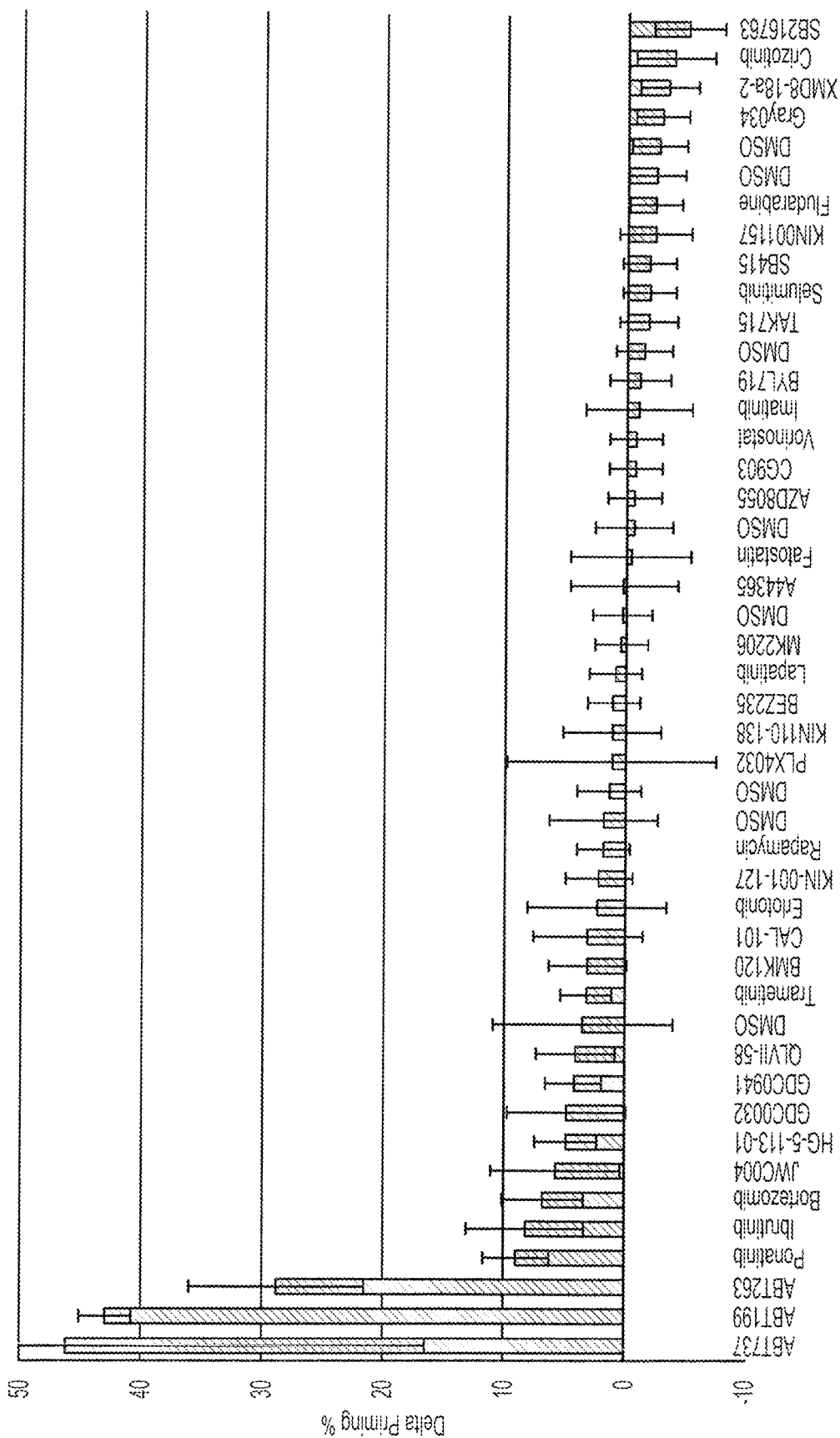
FIG. 22 shows examples of a high throughput dynamic BH3 profile on a select number of drugs on a CLL tumor. The drugs that caused the greater delta priming are those that are likely to increase chemosensitivity. Error bars represent standard deviation.

An example of a high throughput dynamic BH3 profile, and the potential to perform high throughput screens directly on primary tumors using this method on a primary MMTV-PyMT mouse tumors is shown in FIG. 20. Additionally, a high throughput screen is performed on primary ovarian ascites tumors is shown in FIG. 21 and on primary CLL tumors in FIG. 22. Here, the drugs that presumably cause the greatest increase chemosensitivity also produces the greatest increase in delta priming.

What is claimed is:

1. A method of predicting sensitivity of cells to a test agent comprising:
   a) culturing cells attached to an adhesive solid surface in a culture medium having serum in the presence and absence of a test agent;
   b) contacting the cultured attached cells in the culture medium having serum present with a BH3 profiling buffer and a pro-apoptotic BH3 domain peptide;
   c) measuring the amount of BH3 domain peptide induced mitochondrial outer membrane permeabilization (MOMP) in the attached cells in the culture medium having serum present; and
   d) comparing the amount of BH3 domain peptide induced MOMP in the cells cultured in the presence of the test agent to the amount of BH3 domain peptide induced MOMP in the cells cultured in the absence of the test agent,
   wherein an increase in MOMP in the cells cultured in the presence of the test agent compared to the amount of BH3 domain peptide induced MOMP in the cells cultured in the absence of the test agent indicates the cells are sensitive to the test agent.

2. The method of claim 1, wherein the BH3 profiling buffer is added at a concentration of 2×, 3× or 4×.

3. The method of claim 2, wherein the BH3 profiling buffer is added at a concentration of 2× and the amount of BH3 domain peptide induced MOMP is measured by microscopy, or wherein the BH3 profiling buffer is added at a concentration of 3× or 4× and the amount of BH3 domain peptide induced MOMP is measured by Fluorescence-activated cell sorting (FACS).

4. The method of claim 1, wherein the adhesive solid surface is coated with one or more pro-adhesive compounds.

5. The method of claim 4, wherein the one or more pro-adhesive compounds is an extracellular matrix (ECM) protein or an antibody.

6. The method of claim 5, wherein the ECM protein is selected from the group consisting of collagen 1, laminin, collagen 4 and fibronectin, or wherein the ECM protein is an ECM protein mixture derived from animal tissue.

7. The method of claim 1, wherein the BH3 profiling buffer is Derived from Trehalose Experimental Buffer (DTEB) or Mannitol Experimental Buffer (MEB).

8. The method of claim 1, wherein the cells are permeabilized after, prior to, or simultaneously when contacting with the BH3 domain peptide.

9. The method of claim 8, wherein the BH3 profiling buffer is supplemented with a permeabilizing agent, optionally wherein the permeabilizing agent is digitonin or saponin.

10. The method of claim 1, wherein the amount of BH3 domain peptide induced MOMP is measured by FACS, plate fluorimetry, fluorescent imaging or automated image analysis.

11. The method of claim 1, further comprising fixing the cells prior to measuring MOMP, optionally wherein the fixed cells are contacted with an antibody for cytochrome C, SMAC/Diablo, Omi, adenylate kinase-2, apoptosis-inducing factor, Tom20, or VDAC.

12. The method of claim 1, wherein the BH3 domain peptide is derived from the BH3 domain of a BID, a BIM, a BAD, a NOXA, a PUMA a BMF, or a HRK polypeptide.

13. The method of claim 1, wherein the test agent is a therapeutic agent, optionally wherein the therapeutic agent is a chemotherapeutic agent.

14. The method of claim 1, wherein the cells are primary human tumor cells or cells obtained from a patient derived xenograft (PDX).

\* \* \* \* \*

SEQUENCE LISTING

```
<160> NUMBER OF SEQ ID NOS: 17

<210> SEQ ID NO 1
<211> LENGTH: 20
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified by Ac
<220> FEATURE:
<221> NAME/KEY: MOD_RES
<222> LOCATION: (20)..(20)
<223> OTHER INFORMATION: AMIDATION

<400> SEQUENCE: 1
```

Met Arg Pro Glu Ile Trp Ile Ala Gln Glu Leu Arg Arg Ile Gly Asp
1               5                   10                  15

Glu Phe Asn Ala
            20

<210> SEQ ID NO 2
<211> LENGTH: 20
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified by AC
<220> FEATURE:
<221> NAME/KEY: MOD_RES
<222> LOCATION: (20)..(20)
<223> OTHER INFORMATION: AMIDATION

<400> SEQUENCE: 2

Met Arg Pro Glu Ile Trp Ile Ala Gln Glu Leu Arg Arg Ile Gly Asp
1               5                   10                  15

Glu Phe Asn Val
            20

<210> SEQ ID NO 3
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 3

Glu Asp Ile Ile Arg Asn Ile Ala Arg His Leu Ala Gln Val Gly Asp
1               5                   10                  15

Ser Met Asp Arg
            20

<210> SEQ ID NO 4
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 4

Met Arg Pro Glu Ile Trp Ile Ala Gln Glu Leu Arg Arg Ile Gly Asp
1               5                   10                  15

Glu Phe Asn Ala
            20

<210> SEQ ID NO 5
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 5

Glu Asp Ile Ile Arg Asn Ile Ala Arg His Ala Ala Gln Val Gly Ala
1               5                   10                  15

Ser Met Asp Arg
            20

```
<210> SEQ ID NO 6
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 6

Leu Trp Ala Ala Gln Arg Tyr Gly Arg Glu Leu Arg Arg Met Ser Asp
1               5                   10                  15

Glu Phe Glu Gly Ser Phe Lys Gly Leu
            20                  25

<210> SEQ ID NO 7
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 7

Met Glu Gly Ser Asp Ala Leu Ala Leu Arg Leu Ala Cys Ile Gly Asp
1               5                   10                  15

Glu Met Asp Val
            20

<210> SEQ ID NO 8
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 8

Ala Glu Leu Pro Pro Glu Phe Ala Ala Gln Leu Arg Lys Ile Gly Asp
1               5                   10                  15

Lys Val Tyr Cys
            20

<210> SEQ ID NO 9
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 9

Pro Ala Asp Leu Lys Asp Glu Cys Ala Gln Leu Arg Arg Ile Gly Asp
1               5                   10                  15

Lys Val Asn Leu
            20

<210> SEQ ID NO 10
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 10

Ala Ala Gln Leu Thr Ala Ala Arg Leu Lys Ala Leu Gly Asp Glu Leu
1               5                   10                  15

His Gln
```

<210> SEQ ID NO 11
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 11

Glu Gln Trp Ala Arg Glu Ile Gly Ala Gln Leu Arg Arg Met Ala Asp
 1               5                  10                  15

Asp Leu Asn Ala
            20

<210> SEQ ID NO 12
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 12

His Gln Ala Glu Val Gln Ile Ala Arg Lys Leu Gln Leu Ile Ala Asp
 1               5                  10                  15

Gln Phe His Arg
            20

<210> SEQ ID NO 13
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 13

Asn Leu Trp Ala Ala Gln Arg Tyr Gly Arg Glu Leu Arg Arg Met Ser
 1               5                  10                  15

Asp Glu Phe Val Asp Ser Phe Lys Lys
            20                  25

<210> SEQ ID NO 14
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 14

Leu Trp Ala Ala Gln Arg Tyr Gly Arg Glu Ala Arg Arg Met Ser Asp
 1               5                  10                  15

Glu Phe Glu Gly Ser Phe Lys Gly Leu
            20                  25

<210> SEQ ID NO 15
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 15

Arg Pro Glu Ile Trp Met Thr Gln Gly Leu Arg Arg Leu Gly Asp Glu
 1               5                  10                  15

Ile Asn Ala Tyr Tyr Ala Arg
            20

```
<210> SEQ ID NO 16
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 16

Glu Gln Trp Ala Arg Glu Ile Gly Ala Gln Ala Arg Arg Met Ala Ala
1               5                   10                  15

Asp Leu Asn Ala
            20

<210> SEQ ID NO 17
<211> LENGTH: 20
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(10)
<223> OTHER INFORMATION: Xaa can be any amino acid
<220> FEATURE:
<221> NAME/KEY: misc_feature
<222> LOCATION: (12)..(15)
<223> OTHER INFORMATION: Xaa can be any amino acid
<220> FEATURE:
<221> NAME/KEY: misc_feature
<222> LOCATION: (17)..(20)
<223> OTHER INFORMATION: Xaa can be any amino acid

<400> SEQUENCE: 17

Xaa Xaa Xaa Xaa Xaa Xaa Xaa Xaa Xaa Xaa Leu Xaa Xaa Xaa Xaa Asp
1               5                   10                  15

Xaa Xaa Xaa Xaa
            20
```